United States Patent
Niedospial, Jr.

(10) Patent No.: US 6,749,590 B2
(45) Date of Patent: Jun. 15, 2004

(54) SYRINGE BARREL AND PLUNGER ASSEMBLY HAVING ELLIPSOIDAL CONFIGURATIONS

(75) Inventor: John J. Niedospial, Jr., Burlington, NJ (US)

(73) Assignee: Bracco Diagnostics, Inc., Princeton, NJ (US)

( * ) Notice: Subject to any disclaimer, the term of this patent is extended or adjusted under 35 U.S.C. 154(b) by 58 days.

(21) Appl. No.: 09/728,993

(22) Filed: Dec. 4, 2000

(65) Prior Publication Data

US 2003/0097096 A1 May 22, 2003

(51) Int. Cl.⁷ .......................... A61M 5/315; A61M 5/00
(52) U.S. Cl. ..................... 604/218; 604/230; 604/110
(58) Field of Search ................................. 604/218, 264, 604/110, 220, 239, 82, 195, 108, 191, 89, 222, 230; 210/728; 600/486; 222/386

(56) References Cited

U.S. PATENT DOCUMENTS

| 1,222,424 A | * | 4/1917 | Laurent ...................... 604/222 |
| 3,766,918 A | * | 10/1973 | Kessel ...................... 222/386.5 |
| 5,273,543 A | * | 12/1993 | Bell et al. .................... 604/110 |
| 5,411,488 A | | 5/1995 | Pagay et al. ................. 604/218 |
| 5,411,489 A | | 5/1995 | Pagay et al. ................. 604/218 |
| 5,549,573 A | * | 8/1996 | Waskonig ................... 604/218 |
| 5,556,390 A | * | 9/1996 | Hicks ......................... 604/264 |
| 5,700,247 A | | 12/1997 | Grimard et al. ............. 604/220 |
| 5,735,825 A | | 4/1998 | Stevens et al. ............. 604/218 |
| 5,843,043 A | * | 12/1998 | Markus ....................... 604/239 |
| 6,004,300 A | | 12/1999 | Butcher et al. ............. 604/222 |
| 6,017,325 A | * | 1/2000 | Yerfino et al. .............. 604/110 |
| 6,206,859 B1 | * | 3/2001 | Niedospial et al. ......... 604/220 |
| 6,413,236 B1 | * | 7/2002 | Van Dyke ................... 604/110 |

FOREIGN PATENT DOCUMENTS

| EP | 1002551 A1 | 5/2000 |
| GB | 2202747 | 10/1988 |

* cited by examiner

Primary Examiner—Michael J. Hayes
Assistant Examiner—Roz Maiorino
(74) Attorney, Agent, or Firm—M. Caragh Noone; Bryan M. Peckjian

(57) ABSTRACT

A syringe of improved ergonomics having an ellipsoidal barrel which contains an ellipsoidal plunger. The plunger consists of: a plunger tip of a rigid, non-elastomeric material which interfaces a medical fluid contained in the syringe barrel; and an elastomeric ring which slideably interfaces the inside wall of the syringe barrel. In one embodiment the plunger contains a plastic plunger insert which supports the elastomeric ring, the interior of which is provided with an ellipsoidal cavity. A self-aligning plunger rod having a ball portion on its distal end is inserted into the cavity of the plunger insert. The ball portion freely moves in the cavity and directs the external force exerted on the plunger rod in an axial direction.

15 Claims, 19 Drawing Sheets

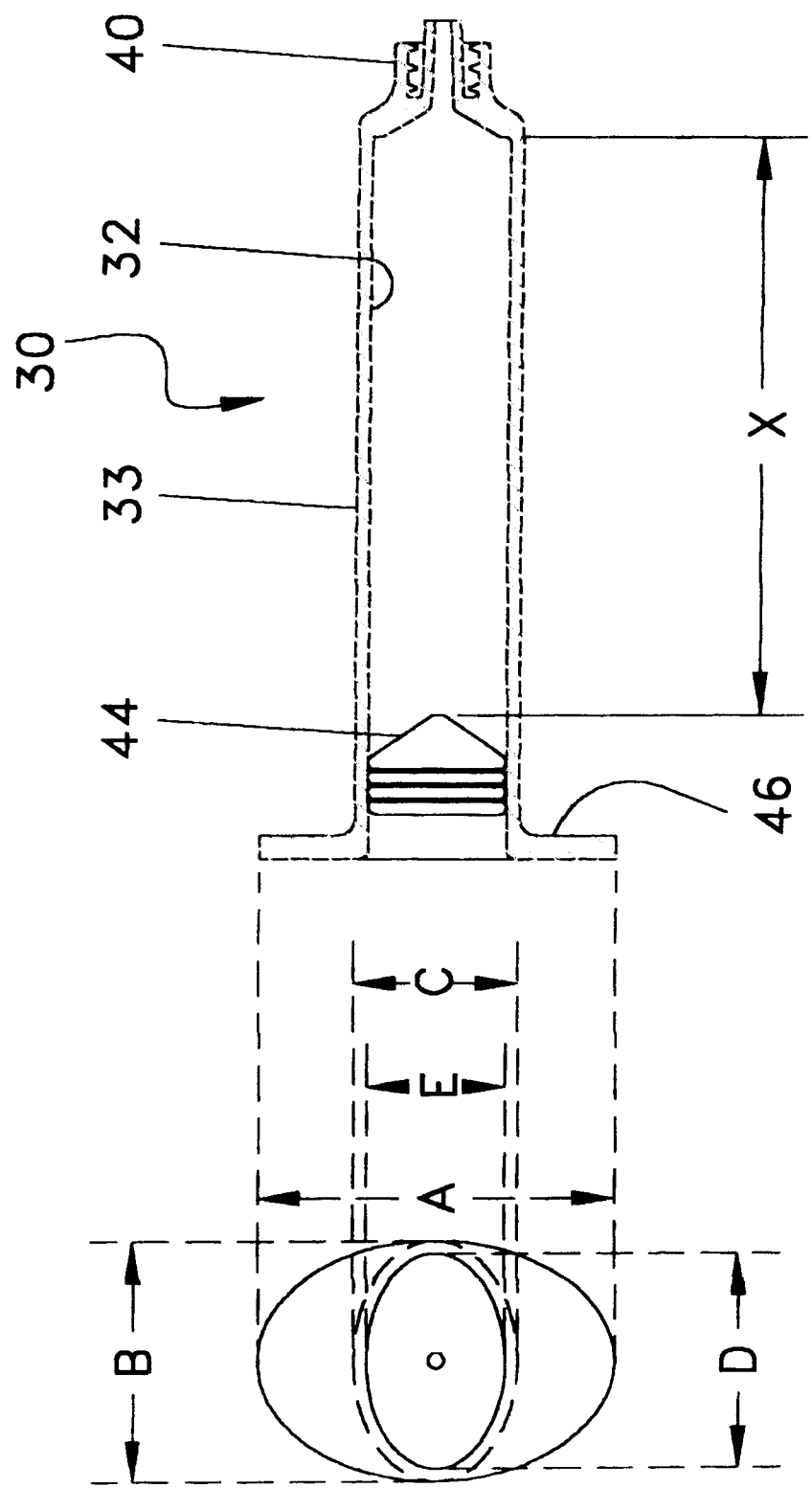

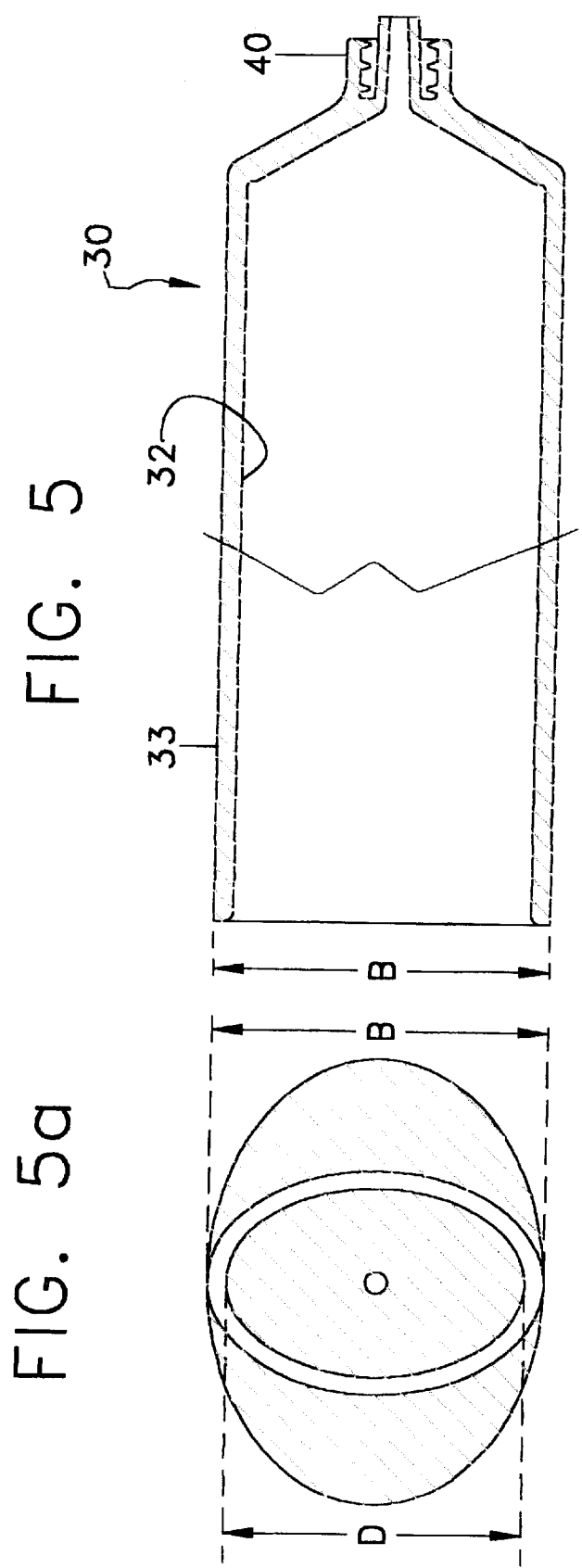

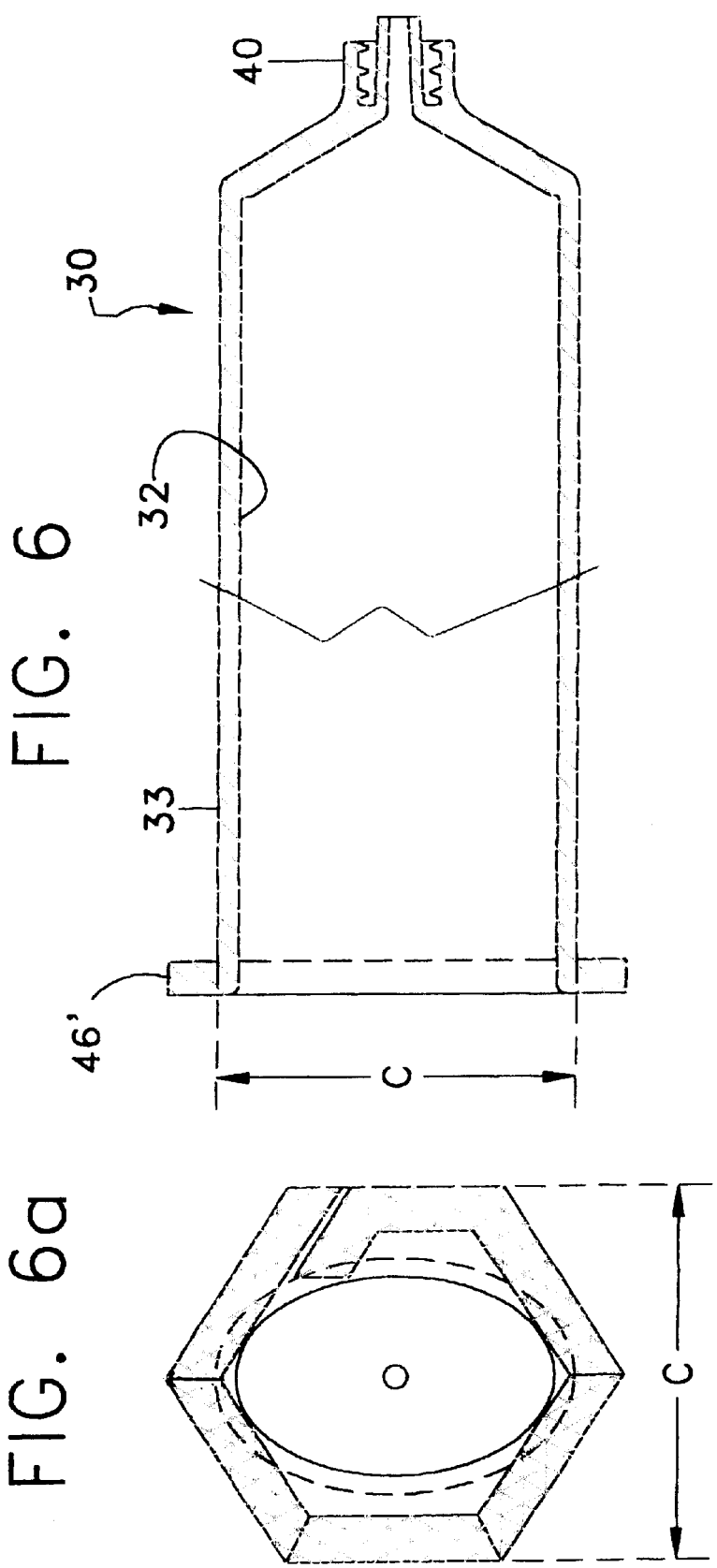

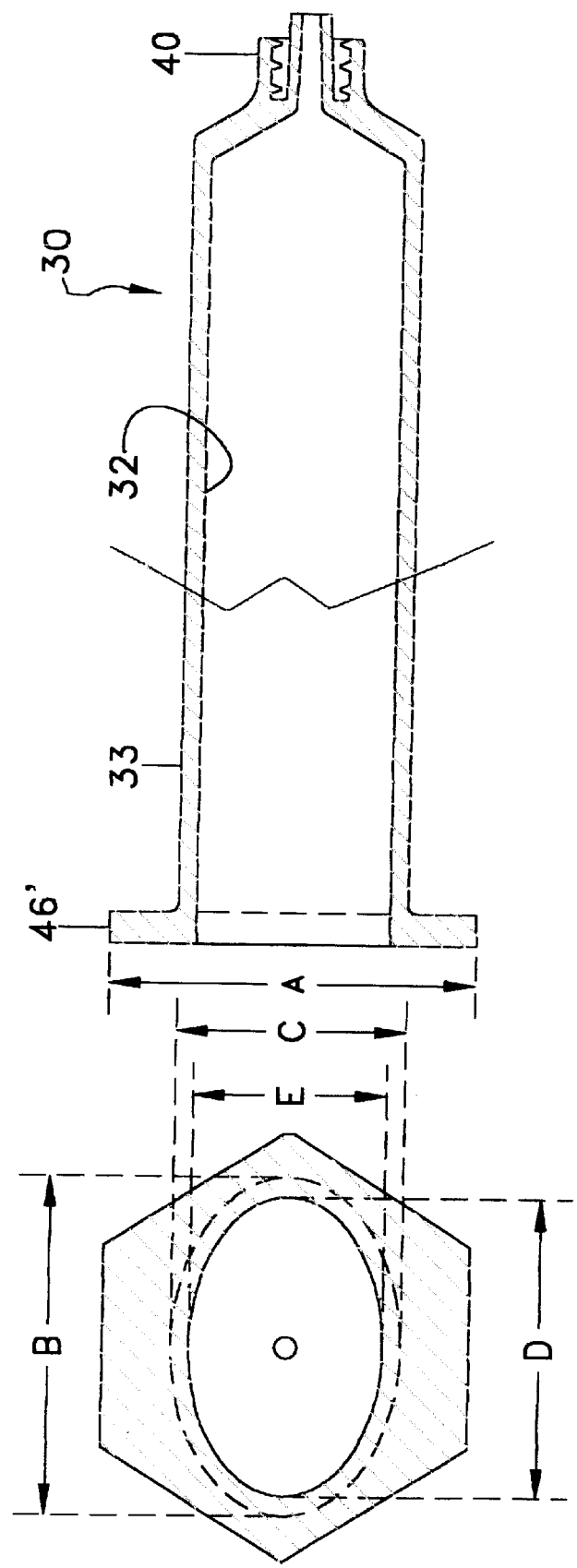

SYRINGE BARREL AND PLUNGER ASSEMBLY HAVING ELLIPSOIDAL CONFIGURATIONS

FIELD OF THE INVENTION

This invention relates to a syringe barrel and plunger assembly having ellipsoidal configurations. More particularly, the invention relates to a syringe barrel and plunger assembly, whose plane sections are all elliptical, wherein the plunger is equipped with a plunger rod or the assembly is used in a power injector with a built-in plunger rod.

BACKGROUND OF THE INVENTION

Hypodermic syringes are well-known in the prior art comprising: a cylindrical syringe body, the horizontal cross-section of which is circular, having a fluid-receiving chamber therein; a proximal end; and a distal end. The distal end of the syringe body tapers into a tip having a bore therethrough which communicates with the fluid-receiving chamber. The top is covered by a closure means such as a stopper of a polymeric or elastomeric material, a tip cap or a membrane to prevent leakage and contamination of the fluid medication contained in the syringe barrel.

Some prior art syringes also include a needle assembly with a needle cannula having a proximal end and a distal end and a lumen extending axially therethrough. The proximal end of the needle cannula is engageable with the tip of the syringe barrel. Other prior art syringes include luer collars spaced around the tips of the syringe barrels. The luer collars include threads for engagement with corresponding threads on the proximal ends of the needle cannulas or IV sets equipped with threads.

A plunger is inserted into the open proximal end of the barrel for sliding in fluid-tight engagement with the inside wall of the fluid-receiving chamber. The plunger is equipped with a plunger rod to enable the user to exert pressure on the plunger which results in the sliding movement of the plunger in the proximal or distal directions.

Prior art syringes of all types, i.e. glass, plastic, reusable, disposable and pre-filled are fabricated with a longitudinal cylindrical configuration and a circular transverse configuration. Among the reasons for this configuration is: the familiarity of medical professionals and the general public with this traditional configuration; easy manufacturing process for round, cylindrical barrels including cutting of threads into the tip of barrels, especially glass barrels; and no orientation is required between the plungers and the barrels during assembly.

Syringes and cartridges made of glass or polymeric material for delivery of fluids to and from a patient have been proposed and utilized by the prior art, and have achieved a highly developed state. Various requirements related to specific delivery systems have also been addressed. While specific requirements of fluid delivery to and from a patient may vary, means of delivery remain essentially the same and may be characterized by the following general description of a syringe.

A syringe comprises:
a) a cylindrical barrel having a proximal end designed for receiving a plunger with or without a plunger rod removably attached to the plunger or being integral with the plunger, and a distal end adapted to mount a needle or luer connector thereon; and
b) a plunger slidably mounted in the barrel.

The plunger is inserted into the barrel at the proximal end of the syringe and thus when fluid is contained in the barrel it may be expelled by pushing the plunger in the barrel towards its distal end; or when the syringe is used to withdraw fluid from a patient, the plunger located at the distal end of the barrel is pulled towards the proximal end of the syringe thereby drawing fluid into the barrel. Since a fluid-tight seal is necessary between the plunger and the inside wall of the barrel, a resilient rubber tip is positioned on the distal end of the plunger, or typically, the plunger is made of resilient rubber-like material. Illustrative examples of prior art syringes and cartridges equipped with plunger/plunger rod units include U.S. Pat. Nos. 5,411,489; 5,531,703; 5,979,668 and 5,735,825.

In order to assure air-tight seal between the inside wall of the syringe barrel and the plunger, prior art plungers are manufactured with a larger outside diameter than the inside diameter of the syringe barrels. When the plunger is introduced into the syringe barrel, it is sufficiently compressed to provide adequate pressure between the inside wall of the syringe and the plunger to seal the interface and withstand the challenges of filling, injecting and withdrawing fluids using the syringe without leakage.

In addition to a leakage-proof seal, another requirement in the syringe/plunger combination is the chemical stability of both the syringe and the plunger. While syringes being made of glass or thermoplastic materials are sufficiently chemically inert to pharmaceutical and biological fluids contained therein, the plungers made of natural rubber or butyl rubber have some undesirable properties. The rubber contains additional chemical components such as fillers and accelerators introduced during the curing process which tend to exude to the surface of the plunger during the contact between the plunger and the fluid contained in the syringe. Such exudate is undesirable in an injection or when a biological fluid, such as blood, is withdrawn from a patient for testing purposes. The problem is further aggravated when there is a long-term storage of the content of the pharmaceutical/biological fluid in the syringe. Recognizing the problem of contamination caused by exudates from plungers made of rubber, the prior art has provided plungers made of thermoplastic materials which do not contain the additives that rubber plungers contain. However, thermoplastic materials are not as resilient as rubbers and the seals formed between thermoplastic plungers and the inside walls of syringes tend to be inadequate in some circumstances. Also, over a period of time on storage the thermoplastic plunger may achieve a compression stage wherein the outside diameter of the plunger is reduced thereby no longer capable of forming a tight seal between it and the inside wall of the syringe.

In addition to the tendency of leakage, the thermoplastic plunger does not slide smoothly in the syringe barrel and requires the exertion of excessive force on the plunger rod to move the plunger in the barrel. The exertion of excessive force on the plunger rod may result in uneven delivery of the fluid to the patient or insertion of the needle into a vein or tissue area to an undesirable depth.

In both the rubber and thermoplastic plungers a relatively large compressive force must be exerted on the plungers by the syringe barrel to provide for a tight, leakproof seal. This quality of the seal, however, makes the movement of the plunger difficult. To remedy the problem the prior art used lubricants to reduce friction and drag between the plunger and the inside surface of the syringe barrel. The use of such lubricants, however, is also undesirable with certain parenteral fluids which tend to disperse or dissolve in the parenteral fluids thereby contaminating the parenteral fluids. Attempts to avoid the use of lubricants included the use of various plunger configurations, such as plungers that were provided with one or more ribs projecting forwardly or rearwardly in the barrel to reduce the frictional drag between the plunger and the inside surface of the barrel.

While fluid tightness and sliding property have improved with these attempts, it appears that improvement in one of these properties is not quite achieved without corresponding decrease in the other property: increasing fluid tightness tends to result in decreasing sliding property, while increasing sliding property tends to result in decreasing fluid tightness.

Prior art plungers, variously designated such as sealing cap, plunger head, cup-shaped plunger, cone-shaped plunger and the like, are constructed of elastomeric materials which in the barrel of a syringe or cartridge interface both the content and the inside surface of the barrel.

In the present invention the plunger is constituted by a rigid, non-elastomeric plunger rod tip which interfaces the content of the barrel, and an elastomeric ring which interfaces the inside surface of the barrel.

The prior art has not adequately addressed the ergonomics of large syringes, i.e. the manner of handling the large syringes during repeated injections in the medical arena. The operating forces, such as breakaway and running forces, associated with large syringes can be taxing on the practitioner without using power assisted syringes.

The present invention is directed to syringes and cartridges having a cylindrical longitudinal configuration and an elliptical transverse configuration. The present invention is not directed to syringes and cartridges having a longitudinal cylindrical configuration and a transverse circular configuration.

The advantages of this configuration include: easy handling by gripping the syringe or cartridge barrel across the narrow, flattened section; allows a simple, positive engagement between the plunger and plunger rod so that the plunger is prevented from rotating in either direction and disengaging from the plunger rod; allows uniquely oriented nesting in power injectors; allows improved labeling, i.e., wider area allows label information such as a package insert printed or placed thereon which facilitates reading of the label information; and allows label information to be printed on the back side of the label which can be read through the opposite side of the wide area.

In addition to providing for good ergonomics by the ellipsoidally configured syringe barrel and plunger, the present invention is also directed to the reduction of breakaway and running forces so that the injections or withdrawal process does not strain the practitioner.

In one embodiment of the present invention a self-aligning plunger rod and plunger insert is used in conjunction with the ellipsoidally configured syringe barrel and plunger to direct the external force exerted on the plunger rod in the axial direction.

SUMMARY OF THE INVENTION

In accordance with one embodiment of the present invention, there is provided a syringe or cartridge barrel (hereinafter sometimes referred to as barrel denoting either or both the syringe barrel or the cartridge barrel) in combination with a plunger or plunger and rod assembly for receiving a medical fluid from a site or for expelling a medical fluid contained in the syringe or cartridge barrel to a site. The medical fluid can be a biological fluid, such as blood, or pharmaceutical fluid such as a diagnostic medium, and a nutritional preparation. The syringe or cartridge barrel and plunger combination comprises:

(a) a barrel of ellipsoidal configuration of glass or polymeric material having an inner surface defining an ellipsoidal chamber for retaining a medical fluid therein, said barrel having:
  (1) a distal end terminating in a tapered tip having a bore therethrough to which an injection needle or a connector equipped with a tubing conduit can be attached; and
  (2) a proximal end for slideably receiving a plunger of ellipsoidal configuration;

(b) a plunger rod having a stem portion and an ellipsoidal head portion which are integral with each other, said head portion being of a rigid, non-elastomeric material, preferably a thermoplastic material, having a distal end, a proximal end, and a generally ellipsoidal shaft therebetween, said ellipsoidal shaft comprising:
  (1) a tip at the distal end thereof adapted for interfacing a medical fluid contained in the ellipsoidal chamber of said syringe barrel; and
  (2) an exterior surface comprising a groove adapted to receive an elastomeric ring;

(c) an elastomeric ring of ellipsoidal configuration having an inside wall and an outside wall, said inside wall defining a vacant ellipsoidal center, said elastomeric ring being positioned on the exterior surface of the ellipsoidal shaft without covering the tip of the plunger rod head comprising:
  (1) a protuberance on the inside wall thereof engaging the groove in the ellipsoidal shaft to form a non-slideable seal therewith; and
  (2) a plurality of rims on the outside wall of the elastomeric ring for interfacing the inner surface of said ellipsoidal barrel to provide a slideable seal between said plunger and said barrel.

The syringe or cartridge barrel preferably also includes a flange of ellipsoidal or hexagonal configuration at its proximal end.

In another embodiment of the present invention the stem portion and the head portion of the plunger rod are separate elements, and accordingly, the syringe or cartridge barrel and plunger combination comprises:

(a) a barrel of ellipsoidal configuration of glass or polymeric material having an inner surface defining an ellipsoidal chamber for retaining a medical fluid therein, said barrel having:
  (1) a distal end terminating in a tapered tip having a bore therethrough to which an injection needle or a connector equipped with a tubing conduit can be attached; and
  (2) a proximal end for slideably receiving a plunger of ellipsoidal configuration;

(b) a plunger rod head of ellipsoidal configuration, said plunger rod head being of a rigid, non-elastomeric material, preferably a thermoplastic material, having a distal end, a proximal end, and a generally ellipsoidal shaft therebetween, said ellipsoidal shaft comprising:
  (1) a tip at the distal end thereof adapted for interfacing a medical fluid contained in the ellipsoidal chamber of said syringe barrel;
  (2) an ellipsoidal inner chamber at the proximal end thereof, said ellipsoidal inner chamber having female spiral threads therein for engaging spiral male threads of a plunger rod stem;
  (3) an exterior surface comprising a groove or recess therein adapted to receive an elastomeric ring having a protuberance thereon;

(c) an elastomeric ring of ellipsoidal configuration having an inside wall and an outside wall, said inside wall defining a vacant ellipsoidal center, said elastomeric ring being positioned on the exterior surface of the ellipsoidal shaft of the plunger rod head, without covering the tip of the plunger rod head, comprising:

(1) a protuberance on the inside wall thereof engaging said groove or recess in the ellipsoidal shafts of the plunger rod head to form a non-slideable seal therewith; and (2) a plurality of rims on the outside wall of the elastomeric ring for interfacing the inner surface of the barrel to provide a slideable seal between the plunger and the barrel;

(d) a plunger rod stem having a distal end and a proximal end comprising:

(1) spiral male threads on the distal end thereof for engaging the spiral female threads in the ellipsoidal inner chamber of the plunger rod head; and (2) a thumb rest on the proximal end onto which external pressure is applied for injecting a medical fluid into a site or withdrawing a medical fluid from a site in operating the syringe.

In another embodiment of the present invention, a syringe or cartridge barrel and plunger combination includes a self-aligning plunger rod and plunger insert assembly for manual or power-assisted withdrawal of a medical fluid from a site or for expelling a medical fluid from the barrel. The combination comprises:

(a) an ellipsoidal barrel;

(b) a self-aligning plunger rod;

(c) an ellipsoidal non-elastomeric plunger insert; and (d) an ellipsoidal plunger ring.

The plunger rod and plunger insert assembly has a self-aligning feature wherein the plunger rod tip fits into the socket of the plunger insert and freely glides therein. This feature allows the plunger rod tip to float in the socket of the plastic plunger insert and eliminates lateral pressure on the plastic plunger insert.

(a) The ellipsoidal barrel comprises:

an ellipsoidal body of glass or polymeric material having an inner surface defining an ellipsoidal chamber for retaining a medical fluid therein, said ellipsoidal body having:

a distal end terminating in a tapered tip having a bore therethrough to which an injection needle or a connector equipped with a tubing conduit can be attached; and a proximal end for slideably receiving a plunger of ellipsoidal configuration.

(b) The self-aligning plunger rod having a distal end and a proximal end comprises:

an end disc at said distal end;

a plunger rod tip extending from said end disc adapted to engage a non-elastomeric plastic plunger insert, said plunger rod tip comprising:

a neck portion; and a ball portion having slots therein extending axially from said neck portion;

a thumb rest at the proximal end of the self-aligning plunger rod for facilitating exertion of an external pressure on said plunger rod.

(c) The ellipsoidal non-elastomeric plunger insert comprising:

an ellipsoidal shaft having a distal end and a proximal end;

at least one ellipsoidal recess between the distal end and the proximal end adapted to hold an elastomeric plunger ring having an ellipsoidal protuberance to engage said ellipsoidal recess;

a cone-shaped head, having an inside surface and an outside surface, extending from the distal end of said ellipsoidal shaft;

an ellipsoidal flange extending from the proximal end of said ellipsoidal shaft;

a first ellipsoidal rim constituting an underside of said ellipsoidal flange;

a second ellipsoidal rim adjacent to said first ellipsoidal rim and projecting slightly above a horizontal surface of said first ellipsoidal rim;

a cavity defined within said second ellipsoidal rim and the inside surface of the cone-shaped head;

a plurality of tabs extending from the second ellipsoidal rim into said cavity; and notches between said tabs to receive said slotted ball portion of said plunger rod tip.

(d) The ellipsoidal plunger ring having an inside wall and an outside wall, said inside wall defining a vacant ellipsoidal center, said inside wall having an ellipsoidal protuberance thereon for engaging said ellipsoidal recess in the non-elastomeric plastic plunger insert; and a plurality of rims on the outside wall for interfacing the inner surface of said ellipsoidal barrel to provide a slideable seal between said ellipsoidal plunger ring and the inside surface of said ellipsoidal barrel.

The syringe or cartridge barrel and plunger combination of the present invention can be used manually or with a power injector.

BRIEF DESCRIPTION OF THE DRAWINGS

FIG. 4 is a longitudinal cross-sectional view of the syringe barrel taken along the line 4—4 of FIG. 2;

FIG. 4a is a cross-sectional view of the syringe barrel and the flange on the syringe barrel taken along the line 4a—4a of FIG. 2;

FIG. 5 is another syringe barrel according to the present invention having a cylindrical configuration in the longitudinal direction, wherein the syringe barrel is not equipped with a flange or a plunger;

FIG. 5a is a cross-sectional end view of the syringe barrel shown in FIG. 5;

FIG. 6 is a cross-sectional view of another syringe barrel according to the present invention having a cylindrical configuration in the longitudinal direction wherein the syringe barrel is equipped with a hexagonal flange;

FIG. 6a is a cross-sectional end view of the syringe barrel shown in FIG. 6;

FIG. 6b is a cross-sectional view of the syringe barrel in the longitudinal direction rotated 90° from that shown in FIG. 6;

FIG. 6c is a cross-sectional end view of the syringe barrel shown in FIG. 6b;

FIG. 7a shows a cross-sectional view of the plunger ring shown in FIG. 7, taken along the line 7a—7a;

DETAILED DESCRIPTION OF THE INVENTION

Figure 1:
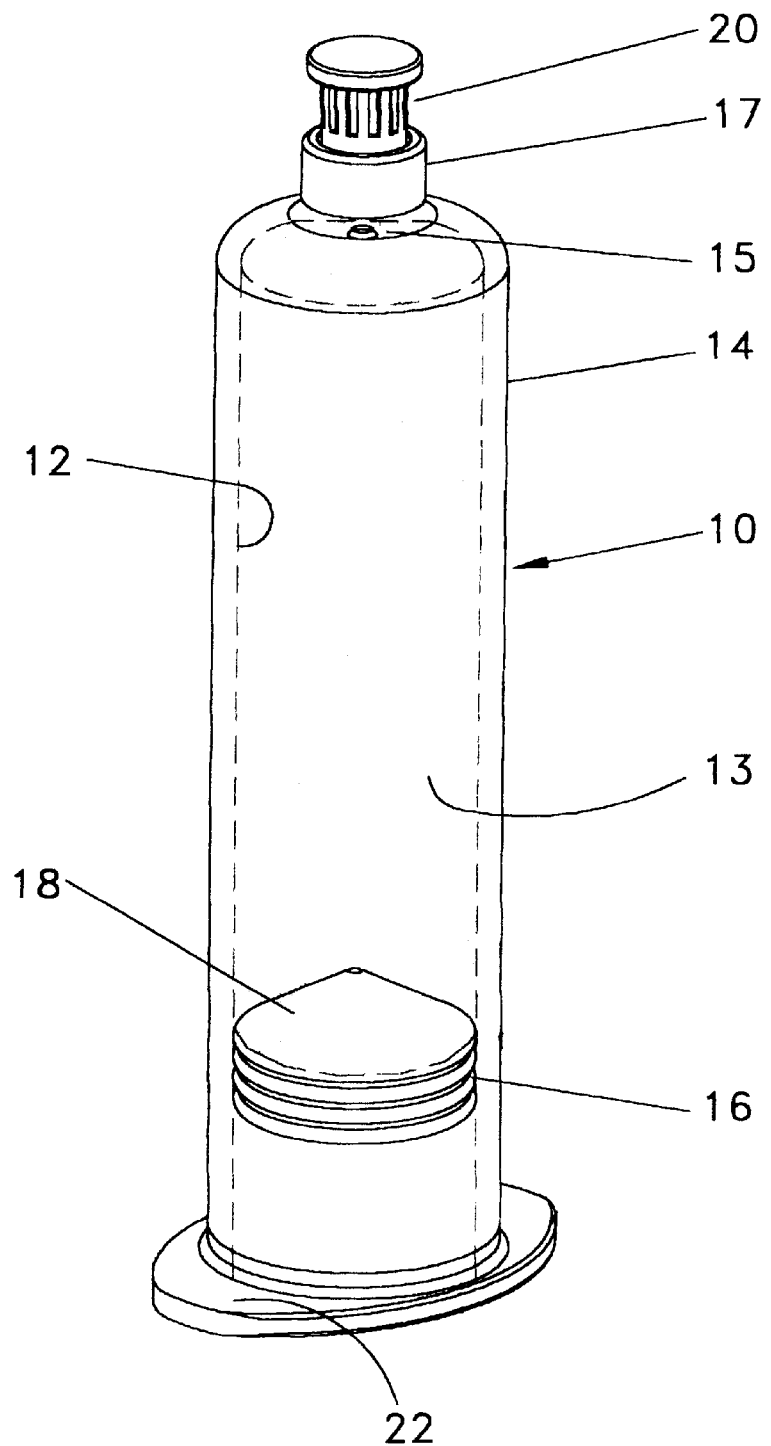
FIG. 1 shows in perspective view a typical prior art cartridge barrel stoppered by an elastomeric closure at the distal end thereof, and a plunger at the proximal end thereof.

FIG. 1 shows the perspective view of a typical syringe or cartridge barrel 10 of the prior art made of glass or polymeric material having an inner surface 12 defining a cylindrical chamber 13 for retaining a medical fluid therein. The barrel has a distal end 14 terminating in a tapered tip 15 having a bore therethrough to which an injection needle or a connector with a tubing conduit can be attached, and a proximal end 16 for receiving a plunger 18 which stoppers the medical fluid in the chamber and which, upon use, expels the fluid from the chamber when an external pressure is exerted thereon. The tapered end having the bore therein is stoppered by an elastomeric closure 20, such as a soft rubber stopper, for hermetically sealing the distal end of the barrel. A luer collar 17 encircles tapered tip 15. At its proximal end the barrel is equipped with a flange 22 to facilitate the handling of the barrel. When the medical fluid is an inject- able solution, the barrel along with its content is sterilized, preferably by autoclave. After sterilization the syringe or cartridge barrel is packaged and stored ready for use when needed.

Figure 1A:
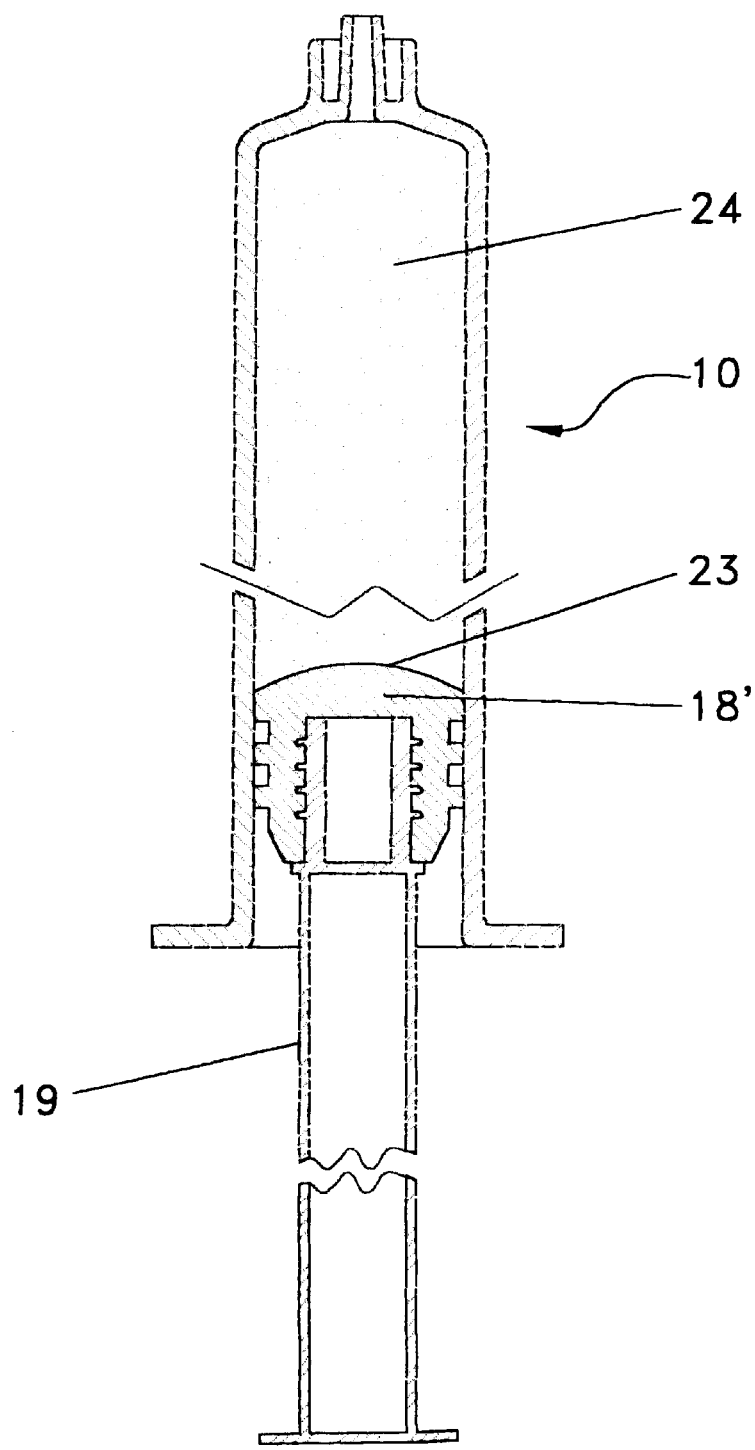
FIG. 1a shows a cross-sectional view of another typical prior art cartridge barrel having a plunger and a plunger rod therein.

FIG. 1a shows a cross-sectional view of another typical prior art syringe barrel having a plunger 18' and a plunger rod 19 therein. The plunger 18' has a smooth semi-circular surface 23 which contacts the medical fluid 24 contained in the syringe barrel.

Figure 2:
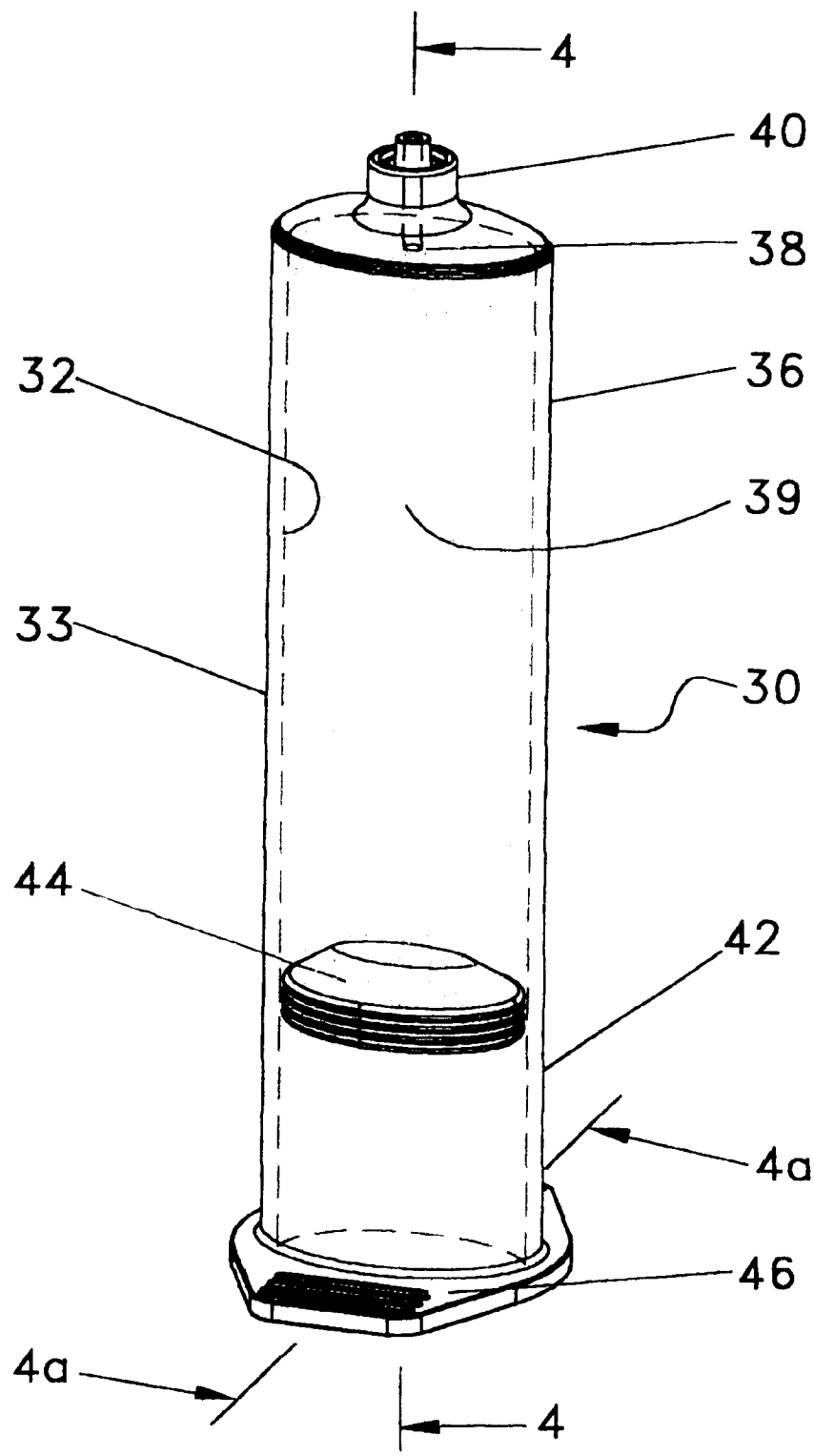
FIG. 2 is a perspective view of the syringe barrel of the present invention having a cylindrical configuration in the longitudinal direction and an elliptical configuration in the transverse direction.

FIG. 2 shows, in perspective view, the syringe barrel of the present invention having a cylindrical configuration, i.e. it is cylindrical longitudinally, and elliptical in the transverse direction. The perspective view in FIG. 2 is identical with the prior art syringe barrel shown in FIG. 1 since the view shows the syringe barrel with its wide transverse configuration facing the viewer.

Figure 3:
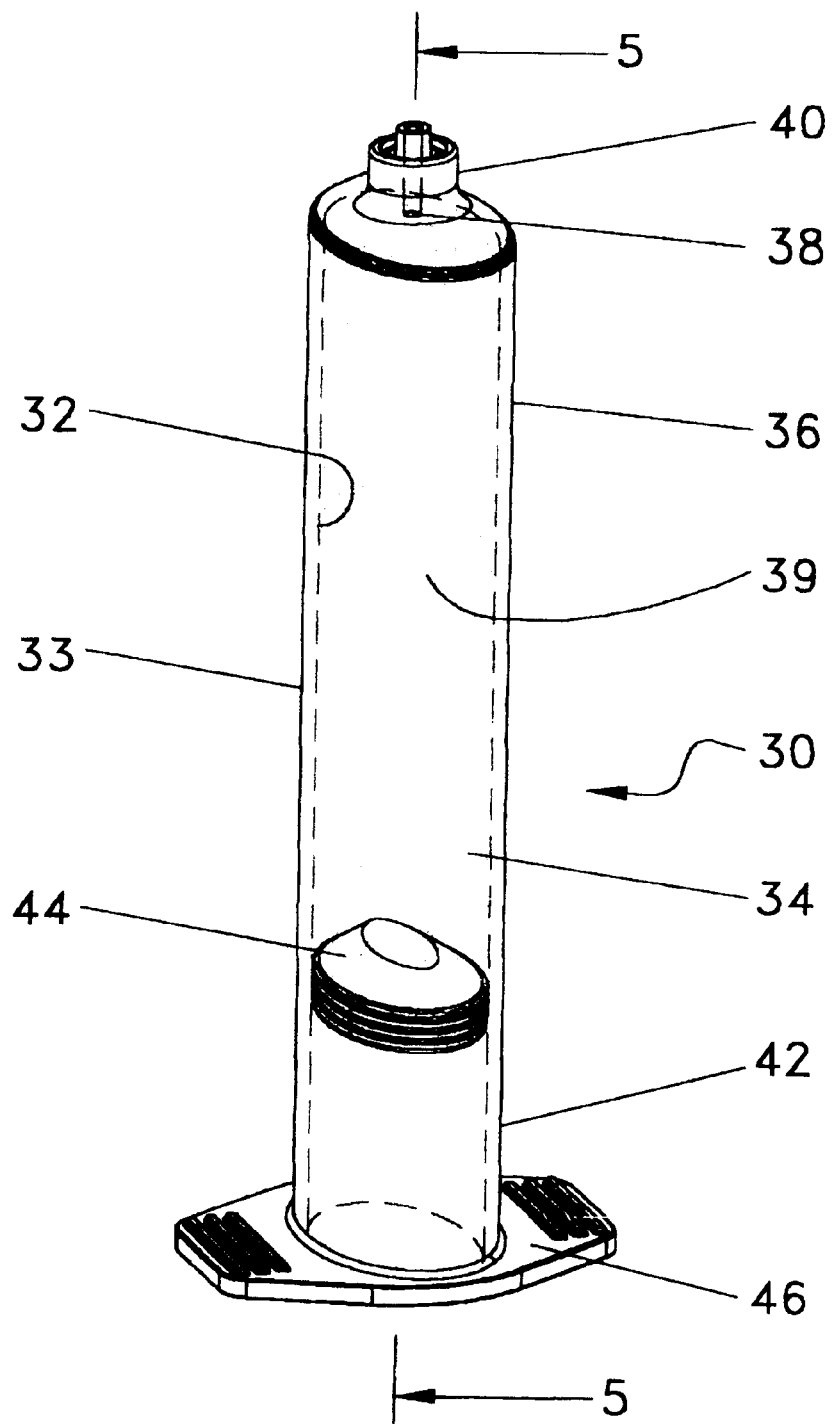
FIG. 3 is a perspective view of the syringe barrel of the present invention shown in FIG. 2 rotated 90° so that the syringe barrel is facing the viewer with its narrow transverse configuration.

FIG. 3 shows, in perspective view, the syringe barrel of the present invention shown in FIG. 2 rotated 90° so that the syringe barrel is facing the viewer with its narrower transverse configuration.

In the figures illustrating the present invention, like numerals refer to identical parts and numerals with superscripts ' refer to like elements and parts.

FIGS. 2 and 3 show a syringe or cartridge barrel 30 made of glass or polymeric material having an inner wall 32 defining a chamber 34 and an outside wall 33. The inner wall and outside wall are cylindrical in the longitudinal direction and elliptical in the transverse direction. The chamber retains a medical fluid 39 therein or any material for syringe dispensing. The volume capacity of the chamber is from about 5 ml to about 500 ml or more, and preferably from 20 ml to 100 ml. The barrel has a distal end 36 terminating in a tapered tip 38 having a bore therethrough. A luer collar 40 encircles tapered tip 38 and serves to receive a corresponding luer connector of a syringe, or a luer connector of an IV set with tubing conduit. The barrel has a proximal end 42 for receiving a plunger 44 which stoppers the medical fluid in the chamber and which, upon use, expels the fluid from the chamber when an external force is exerted thereon. At its proximal end the barrel is equipped with a flange 46 to facilitate the handling of the barrel. The barrel containing the medical fluid is sterilized, preferably by autoclave. After sterilization the syringe or cartridge barrel is packaged and stored ready for use when needed.

FIG. 4 is a longitudinal cross-sectional view of the syringe barrel taken along the line 4—4 of FIG. 2, while FIG. 4a is a cross-sectional view of the syringe barrel taken along the line 4a—4a of FIG. 2. In FIG. 4: the numeral 30 denotes the cartridge barrel; the numeral 40 denotes the luer collar; the numeral 32 denotes the inner wall of the cartridge barrel; the numeral 33 denotes the outside wall of the cartridge barrel; the numeral 46 denotes the flange on the proximal end of the barrel; the letter X denotes the effective length of the syringe barrel; and the numeral 44 denotes the plunger.

In FIG. 4a the cross-sectional view of the syringe barrel shows a typical ellipse having two diameters: one being the long diameter, hereinafter referred to as the longitudinal axis of the ellipse; and a short diameter perpendicular to the long diameter, hereinafter referred to as the transverse axis of the ellipse. In the cross-sectional view shown the following identifiers are used:

A=longitudinal axis of the flange;
B=transverse axis of the flange;
B=longitudinal axis of the barrel;
C=transverse axis of the barrel;

D=longitudinal axis of the chamber; and

E=transverse axis of the chamber.

It is to be noted, as shown in the drawing in FIG. 4a, that the transverse axis of the elliptical flange has the same length as the longitudinal axis of the elliptical barrel.

By varying the longitudinal axis and/or the transverse axis of the ellipse, the configuration thereof may be changed from a circle, wherein the longitudinal axis and transverse axis are equal) to a rather flat ellipse wherein the longitudinal axis is equal to that of a circle, and the transverse axis approaches zero. Preferably, however, the dimensions of the longitudinal and transverse axes should be such that the surface area of the ellipse equals or at least approximates the surface area of a circle. In order to vary the area enclosed by a circle, the following formula may be used:

$$\text{Area of circle} = \pi \cdot r^2$$

where r is the radius of the circle.

Knowing the area of a circle, an ellipse with a matching area can be calculated by inserting the circle's area and the dimensions of D or E in formula 1 or 2:

$$D = \frac{\text{area of circle}/\pi}{E} \qquad 1)$$

$$E = \frac{\text{area of circle}/\pi}{D} \qquad 2)$$

When both D and E are known, the area can be calculated by formula 3:

$$\text{Area of circle} = \tfrac{1}{2}E \cdot \tfrac{1}{2}D \cdot \pi \qquad 3)$$

For a preferred cross-sectionally elliptic syringe barrel of 50 ml volume capacity, D is about 1.464 inches and E is about 0.750 inches. Using these dimensions, the elliptical cross-sectional area is about the same as a circle having a radius of about 0.524 inches and dimension E equals that of a 20 mL round syringe.

The wall thickness of the cross-sectionally elliptic syringe barrel may be of from about 0.02 to about 0.10 cm, and preferably about 0.08 cm. The ratio of the longitudinal axis B and the transverse axis C of the cross-section of the elliptical barrel can be from about 1.0 to 0.5 unit or less. It has been observed that when the transverse axis C is less than 0.5 unit structural integrity of the syringe barrel decreases unless compensated by thicker barrel walls. The preferred ratio, therefore, is of from about 1.0 unit for B to about 0.6 unit for C. Also, this ratio closely approximates the cross-sectional area of a syringe barrel having a circular cross-section thereby allowing an engineer to maintain the same barrel length as in a conventional syringe barrel.

FIG. 6 is another syringe barrel of the present invention having a cylindrical configuration in the longitudinal direction wherein the syringe barrel is equipped with a hexagonal flange. In the figure: the hexagonal flange is denoted by the numeral 46', the outside wall is denoted by the numeral 33, the inner wall is denoted by the numeral 32, the luer collar is denoted by the numeral 40, and the transverse distance between the outside walls is denoted by the letter C.

FIG. 6a is a cross-sectional end view of the syringe barrel shown in FIG. 6 wherein C denotes the transverse distance between the outside walls of the barrel.

FIG. 6b is a cross-sectional view of the syringe barrel in the longitudinal direction rotated 90° from that shown in FIG. 6 wherein: A denotes the longitudinal axis of the flange, the numeral 33 denotes the outside wall of the syringe barrel, the numeral 32 denotes the inside wall of the syringe barrel, the numeral 40 denotes the luer collar, and the numeral 46' denotes the flange.

FIG. 6c is a cross-sectional end view of the syringe barrel shown in FIG. 6b wherein: B denotes the longitudinal axis of the barrel, C denotes the transverse axis of the barrel, E denotes the transverse axis of the chamber, and D denotes the longitudinal axis of the chamber.

The syringe barrel of the present invention having an elliptical cross section and a cylindrical longitudinal configuration, hereinafter sometimes referred to as an ellipsoidal syringe barrel, requires a plunger of similar ellipsoidal configuration. Plunger 18 shown in FIG. 1 and plunger 18' shown in FIG. 1A are illustrating typical prior art plungers which may be used if configured as ellipsoids.

For improved ergonomics it is important that not only the physical shape of the syringe barrel be changed from the traditional cylindrical syringe barrel to the ellipsoidal syringe barrel, but also the breakaway and running forces be reduced in the syringe barrel. In addition to reducing these forces, the contact between an elastomeric plunger and the medical fluid contained in the syringe barrel should be reduced as much as possible so that undesirable trace components contained in the elastomeric plunger would not leach into and contaminate the medical fluid.

Figure 7:
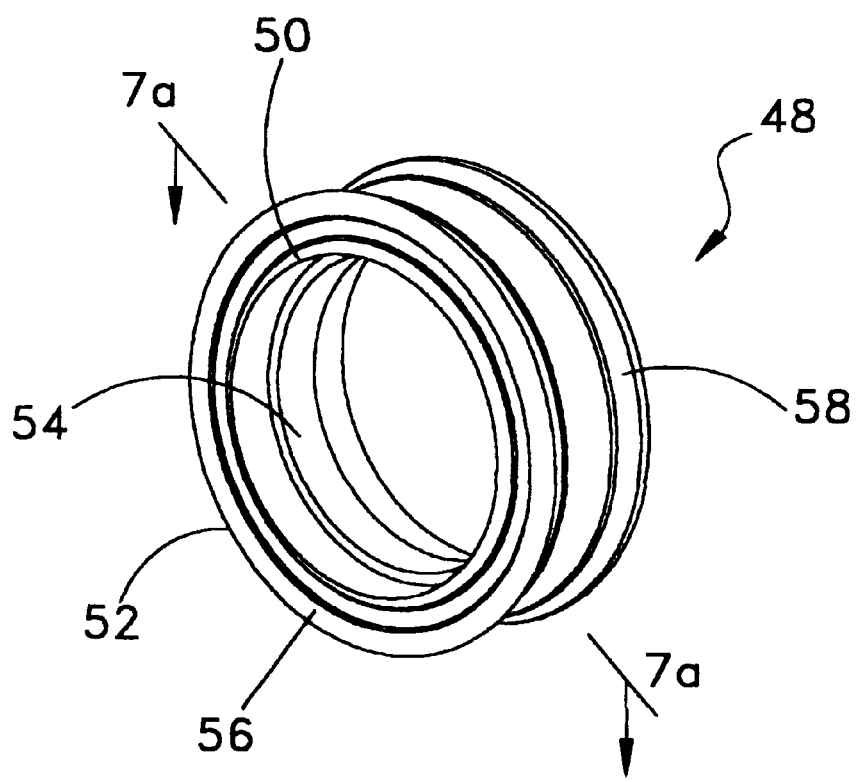
FIG. 7 shows a perspective view of a plunger ring of the present invention.

FIG. 7 shows an elastomeric plunger ring in a perspective view which is used as a component of the present invention replacing the typical elastomeric plunger. The elastomeric plunger ring comprises an inside wall 50 and an outside wall 52, wherein the inside wall forms an ellipsoidal cylinder with a vacant center 54, the cylinder being vacant at the proximal end 56 and the distal end 58 as well as between the proximal end and the distal end thereof. Inside wall 50 comprises internal protuberance which protrudes toward the vacant center 54 of the elastomeric plunger ring designed to engage a recess or groove on a cylindrical shaft of a plunger rod thereby to form a non-slideable engagement between the plunger ring and the plunger rod.

Figure 7A:
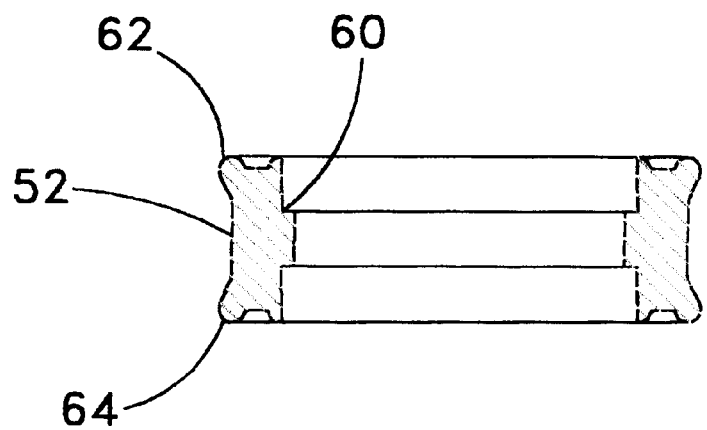

FIG. 7a shows a cross-sectional view of the plunger ring shown in FIG. 7, taken along the line 7a—7a, wherein: an inside wall 50 comprises internal protuberance 60 which protrudes towards the vacant center 54 of the elastomeric ring 48 designed to engage a cylindrical recess or groove on a shaft of a plunger rod; an outside wall 52 having a first rib 62 at the distal end thereof, and a second rib 64 at the proximal end thereof. The configuration of the first and second ribs are smooth, semi-circular projecting away from the outside wall 52 towards the inside wall of a cartridge barrel.

Figure 7B:
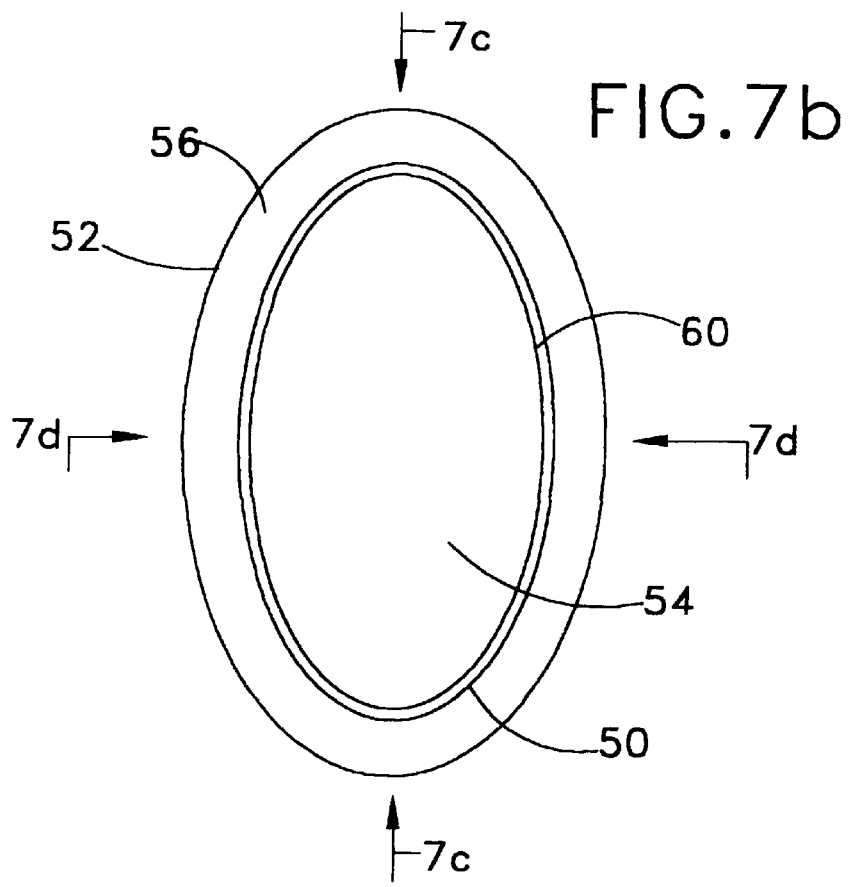
FIG. 7b shows the elliptical cross-sectional end view of the plunger ring shown in FIG. 7.

FIG. 7b shows an elliptical cross-sectional end view of the plunger ring of FIG. 7 wherein: 50 denotes the inside wall; 52 denotes the outside wall, 54 denotes the vacant center, 56 denotes the proximal end, and 60 denotes the internal protuberance.

Figure 7C:
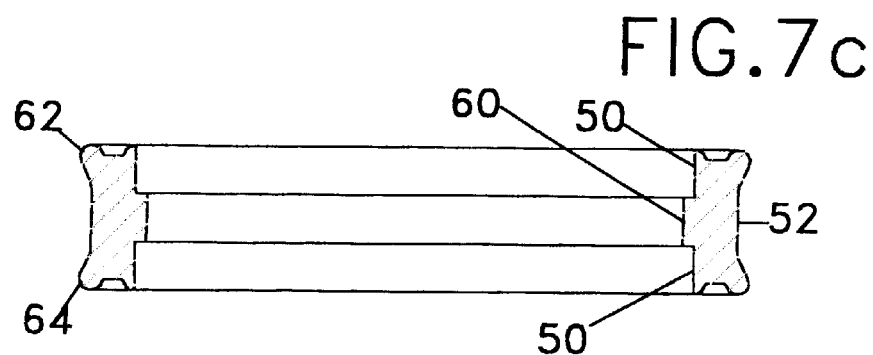
FIG. 7c shows a cross-sectional view of the elliptical end view of FIG. 7b, taken along the line 7c—7c of FIG. 7b.

FIG. 7c shows a cross-sectional view of the elliptical cross-sectional end view of FIG. 7b taken along the line 7c—7c of FIG. 7b.

Figure 7D:
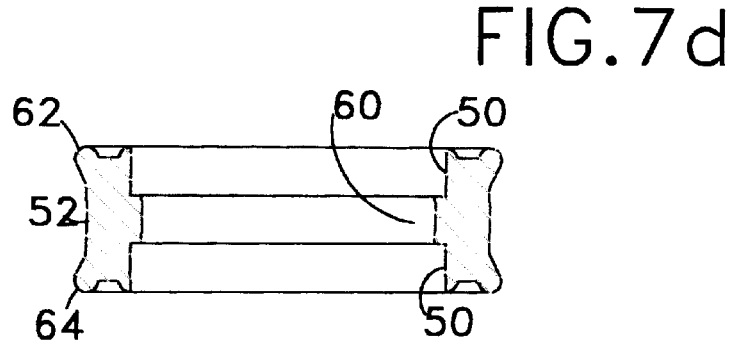
FIG. 7d shows a cross-sectional view of the elliptical cross-sectional end view of FIG. 7b, taken along the line 7d—7d.

FIG. 7d shows a cross-sectional view of the elliptical cross-sectional end view of FIG. 7b taken along the line 7d—7d of FIG. 7b.

The numerals in FIGS. 7c and 7d denote the same elements as in FIG. 7b.

The ellipsoidal plunger ring of the present invention requires a support means onto which the plunger ring is positioned. The support means is a plunger rod having a plunger head. The plunger head may be integral with the plunger rod or it may be removably attached to the plunger rod.

Figure 8:
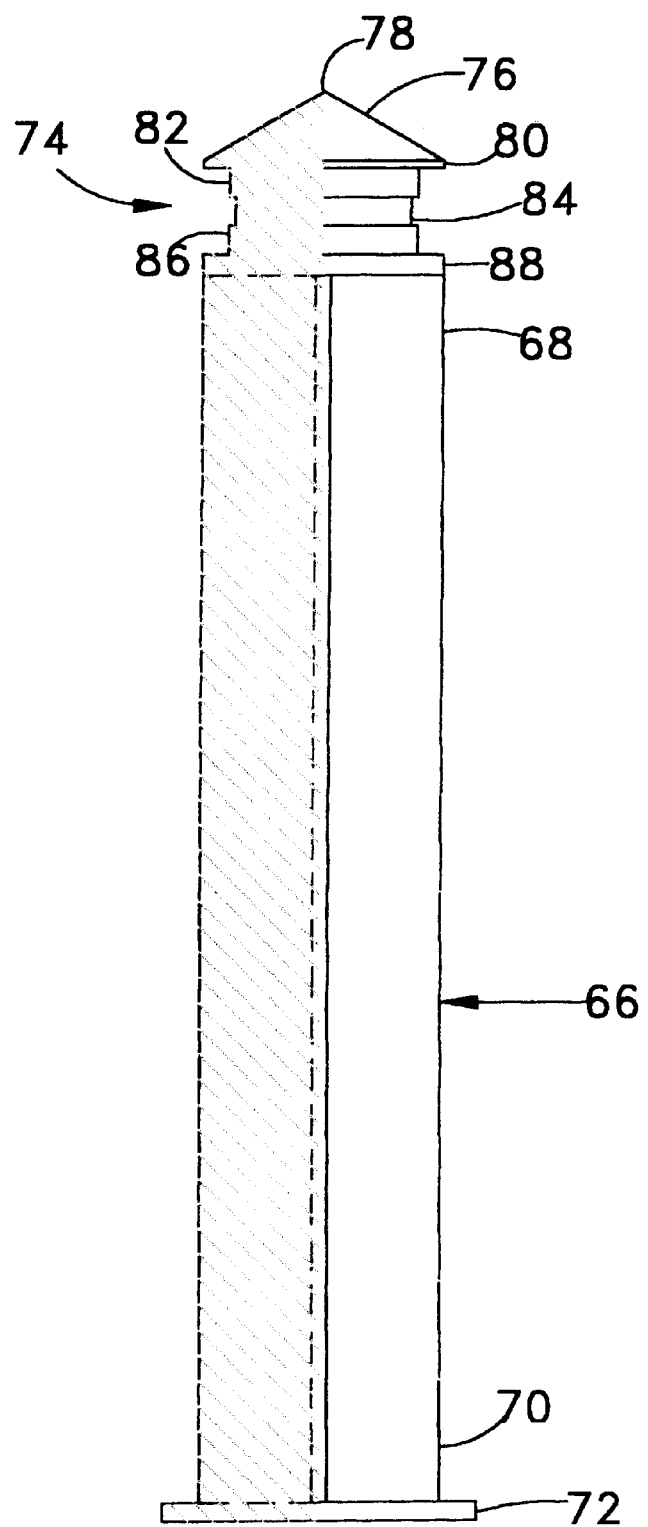
FIG. 8 is a perspective view of a plunger rod, without the plunger rod head, showing threads on the distal end thereof.

FIG. 8 shows in a cross-sectional view a plunger rod which is integral with the plunger rod head. Plunger rod, generally designated at 66, comprising: a distal end 68, a proximal end 70, and a thumb rest 72 at the proximal end of the plunger rod. At the distal end 68 of the plunger rod, and integral with the plunger rod, there is provided a plunger rod head, generally designated at 74, which comprises: a tip 76 which can be flat, or mushroom-shaped, terminating in a zenith 78; a flange 80 on the bottom end of the tip; side portions 82 and 86 projecting towards the plunger rod from the flange; a recess or groove 84 between side portions 82 and 86, and a bottom shoulder portion of the side portion connecting side portion 86 with distal end 68 of plunger rod 66.

Plunger ring 48 is positioned on plunger rod head 74 by placing the plunger rod head into the vacant center 54 of the plunger ring. The inside wall 50 of the plunger ring faces the side portions 82 and 86 of the plunger rod head; protuberance 60 on the inside wall of the plunger ring fits into recess or groove 84 in the plunger rod head 74 and will remain secured thereon due to the elastomeric nature of the plunger ring. Side portions 82 and 86 of the plunger rod head will be engaged by the inside wall 50 of plunger ring between the flange 80 and bottom shoulder 88 of the plunger rod head.

As used herein, plunger rod head denotes a rigid, non-elastomeric, and preferably a thermoplastic, generally cylindrical or ellipsoidal body or disc that fits snugly into a syringe or cartridge barrel without providing a leakproof seal for a medical fluid contained in the syringe or cartridge barrel. The plunger head moves back and forth in the barrel under external pressure exerted thereon during the injection process and during withdrawal of a medical fluid from a site. The plunger head tip has at least 95% contact or interface with the medical fluid contained in the barrel of a syringe or a cartridge. The elastomeric plunger ring positioned on the rigid thermoplastic ring, without covering the plunger rod head tip, has about 5% or less contact or interface with the medical fluid contained in the barrel of a syringe or cartridge. It is designed to contact the inner surface of the barrel to provide a tight, effective, slideable seal between the elastomeric ring and the inner surface of the barrel. The minimal contact between the elastomeric ring and the medical fluid content of the cartridge barrel is highly desirable for the reason that elastomeric materials contain trace amounts of substances which can leach into the medical fluid and contaminate the same especially if silicone or other lubricant is used in the elastomeric material.

The present invention provides for easy starting of the plunger in the syringe barrel, commonly referred to as "breakaway force", and easy forward and reverse movement of the plunger in the cartridge barrel, commonly referred to as "running force". Comparative tests were conducted between the present invention and a typical syringe barrel to determine the breakaway and running forces required to operate a syringe. The results of testing is shown in Table I.

TABLE I 20 ml Syringe Test Data

|  | Present Invention | Prior Art |
| --- | --- | --- |
| Breakaway Force with Silicone | 0.15 lbs | 4.3 lbs |
| Breakaway Force without Silicone | 0.61 lbs | 16.9 lbs |

TABLE I-continued 20 ml Syringe Test Data

|  | Present Invention | Prior Art |
| --- | --- | --- |
| Running Force with Silicone | 0.17 lbs | 2.5 lbs |
| Running Force without Silicone | 0.60 lbs | 11.6 lbs |
| Leakage | None | some observed between plunger ribs |
| Test to Failure (Breakage) | 100.0 lbs | 86.0 lbs |

The low breakaway and running forces greatly contribute to the ergonomics of the present invention.

Materials of Construction

The ellipsoidal syringe barrel of the present invention in this and other embodiments thereof is made of an inert gas impermeable, substantially transparent material, such as cyclic olefin copolymers, polymethylpentene, polyethylene, polypropylene, polystyrene, acrylic and methacrylic polymers and glass.

The elastomeric ellipsoidal plunger ring is made of compressible, elastomeric: materials including:

natural rubber;

acrylate-butadiene rubber;

cis-polybutadiene;

chlorobutyl rubber;

chlorinated polyethylene elastomers;

polyalkylene oxide polymers;

ethylene vinyl acetate;

fluorosilicone rubbers;

hexafluoropropylene-vinylidene fluoride-tetrafluoroethylene terpolymers, such as sold under the tradenames of Fluorel and Viton;

butyl rubbers;

polyisobutene, such as sold under the tradename Vistanex;

synthetic polyisoprene rubber;

silicone rubbers;

styrene-butadiene rubbers;

tetrafluoroethylene propylene copolymers; and thermoplastic-copolyesters.

The durometer of the various elastomeric materials should preferably be in the range of from about 25 to about 80 Shore A.

The plunger rod head including the plunger rod tip and the plunger rod is made of polyethylene, polypropylene, polystyrene, acrylic polymers and methacrylic polymers.

The plunger rod head, instead of being integral with a plunger rod, may be a separate element in the present invention. In this embodiment the plunger rod head is removeably attached to a plunger rod 90.

Figure 9:
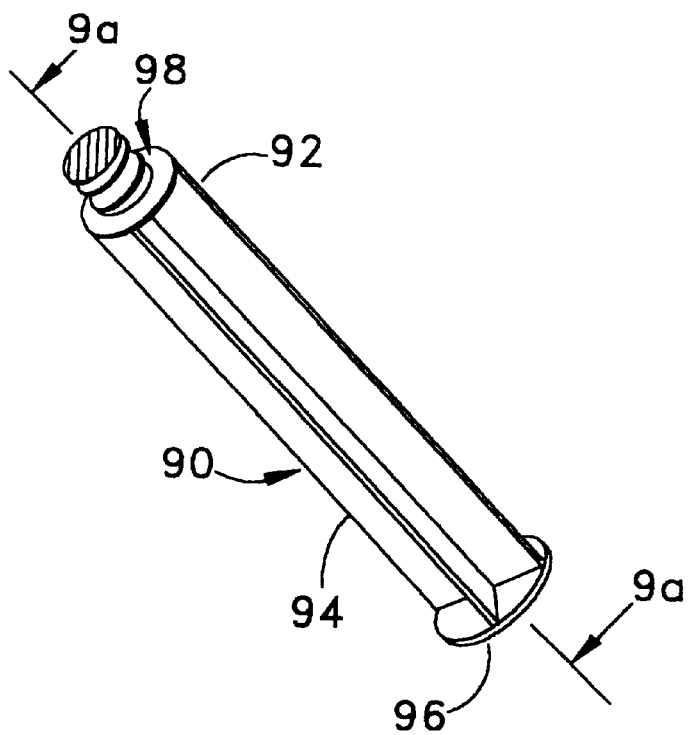
FIG. 9 shows a plunger rod in a perspective view.
Figure 9A:
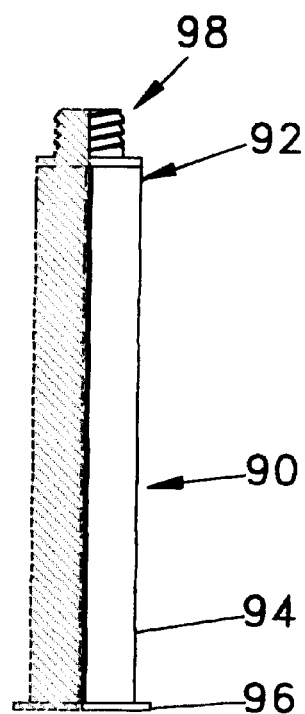
FIG. 9a shows the plunger rod in a cross-sectional view taken along the line 9a—9a of FIG. 9.

Plunger rod 90 is shown in a perspective view in FIG. 9 and in cross-sectional view 9a taken along the line 9a—9a of FIG. 9, wherein: the plunger rod has a distal end 92 and a proximal end 94. At the proximal end the plunger rod is equipped with thumb rest 96, while at the distal end the plunger rod terminates in male spiral threads 98. Prior to use the plunger rod head 74 having female spiral threads thereon is engaged with the plunger rod 90 by rotating the plunger rod into the plunger rod head.

Figure 10:
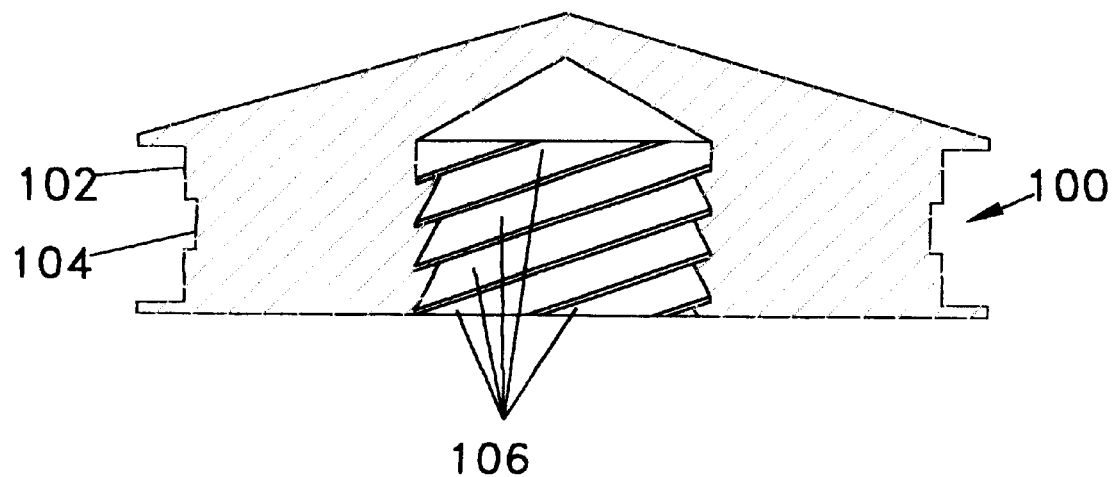
FIG. 10 shows a cross-sectional view of a plunger rod head.
Figure 10A:
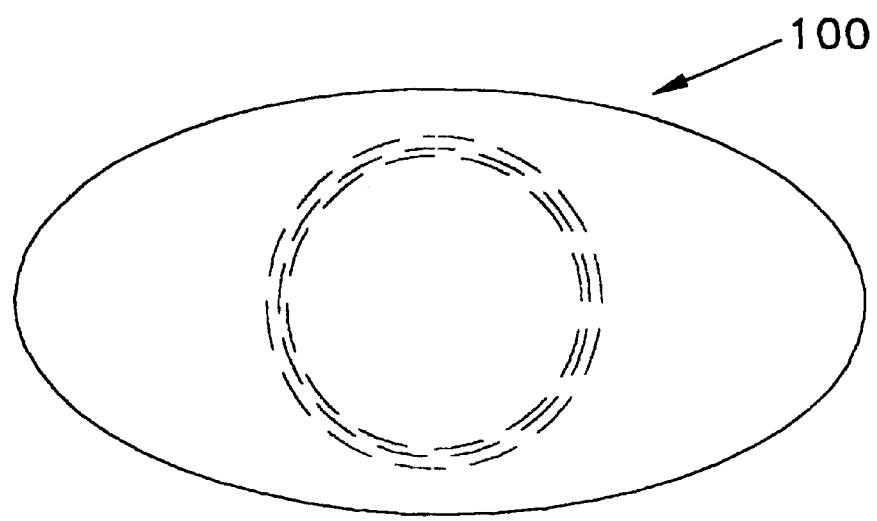
FIG. 10a shows a top plan view of the plunger rod head.

The plunger rod head 100 as a separate element in accordance with the present invention is shown in longitudinal cross-section and top plan views respectively, in FIGS. 10 and 10a wherein: the plunger rod head is provided with a recess or groove 104 on the outside wall 102 for receiving the internal protuberance 60 of plunger ring 48. The plunger rod head is also equipped with internal female spiral threads 106 for attachment to the plunger rod 90 via the spiral male threads on the plunger rod head 100.

Figure 11:
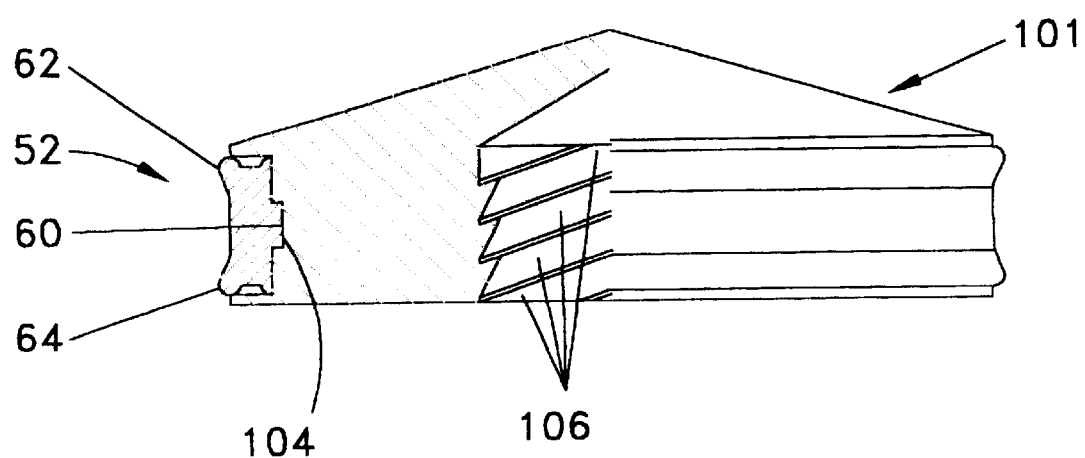
FIG. 11 shows in a longitudinal cross-sectional view an assembled plunger rod head with an elastomeric ring.
Figure 11A:
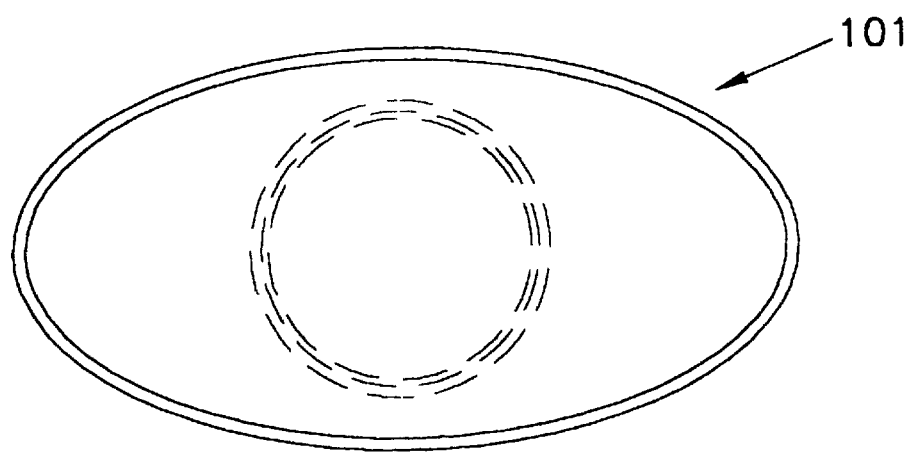
FIG. 11a shows a top plan view of the assembled plunger rod head with the elastomeric ring shown in FIG. 11.

FIGS. 11 and 11a show in longitudinal cross-sectional and top plan views an assembled plunger rod head with an elastomeric ring positioned on the plunger rod head designated generally at 101, wherein: the plunger rod head closely resembles the plunger rod head shown in FIGS. 10 and 10a, and the elastomeric plunger ring is as shown in FIGS. 7, 7a, 7b, 7c and 7d. The plunger rod head 100 comprises: internal spiral female threads 106 for engagement with male spiral threads 98 of plunger rod 90; outside wall 102 having a recess or groove 104 therein for non-slideable engagement with internal protuberance 60 on plunger ring 48. The plunger ring comprises: outside wall 52 having a proximal end 56, and a distal end 58, an internal protuberance 60 for engagement with recess or groove 104 on the outside wall of the plunger rod head 100; first rib 62 and second rib 64 on the outside wall of the plunger ring designed to form a slideable engagement with the inside wall of a syringe barrel. The two ribs provide a tight, slideable seal when the plunger ring/plunger rod head assembly is moved in the barrel in the proximal or distal direction.

In a preferred embodiment of the present invention the plunger rod head and plunger ring assembly has an advantageous self-aligning feature. This self-aligning feature has not been adequately addressed by the prior art which will be referred to as the description of the invention proceeds.

In using a syringe for injection, the force applied to the plunger by the plunger rod should be perpendicular to the plunger so that the force exerted on the wall of the barrel by the plunger is uniform around the 360° of its cylindrical configuration. When the plunger rod flexes in the barrel, the direction of force on the plunger will not be uniform resulting in pressure points at certain areas of contact between the plunger and the inside wall of the barrel and, conversely, inadequate pressure points at other parts of the interface between the plunger and the inside wall of the barrel. Such pressure differences tend to allow leakage and difficulty in moving the plunger at an even rate in the barrel.

Typical prior art devices have fixed connections between plunger rods and plungers; they are either one-piece combinations of plunger rods and plungers or two-piece combinations wherein the plunger rods are threaded into the plungers. Some plungers are equipped with rigid plastic inserts having internal threads therein in order to support the elastomeric plunger heads and to engage the plunger rods and hold them in an axial orientation. Both approaches allow some movement of the plunger rods in a lateral direction which may result in leakage of the medical fluid from the syringe barrel.

Recognizing the importance of dimensional stability, the prior art has incorporated various stability enhancing means into plunger rods which include the following.

A plunger rod, the central portion of which is almost as large as the inside diameter of the syringe barrel so that it will assist in keeping the plunger rod assembly concentrically aligned within the syringe barrel.

A shank having a plurality of longitudinal and radially extending vanes. In one preferred embodiment the shank is provided with four vanes in an "X" pattern, while in another preferred embodiment, the shank is provided with three vanes forming a "Y" pattern.

Plunger rods having a plurality of vanes or support ribs.

A common feature of these plunger rods is a shank extending between the distal and proximal ends of the plunger rods having vanes or support ribs thereon. The vanes or support ribs are identical with one another running longitudinally on the shank and extending radially therefrom. This feature provides the plunger rods with limited flexibility in the lateral direction, thereby exerting pressure on the plunger surface in an axial direction. However, we have found that even limited flexibility of the plunger rods allow lateral movement of the plungers in syringe barrels. This lateral movement of the plunger rods attached to plungers can cause leakage of fluid from the syringe barrels.

The present invention provides a plunger rod and plastic plunger insert combination for an ellipsoidal plunger ring wherein said combination directs the force exerted on the plunger rod in an axial direction. The elastomeric plunger ring placed on the plastic plunger insert will exert a uniform force on the inside wall of the ellipsoidal syringe barrel thereby preventing leakage of the fluid content from the ellipsoidal syringe barrel.

Reference is now made to FIGS. 12, 13, 14 and 15 showing perspective, side-elevational, bottom and top plan views of a self-aligning plunger rod.

Figure 12:
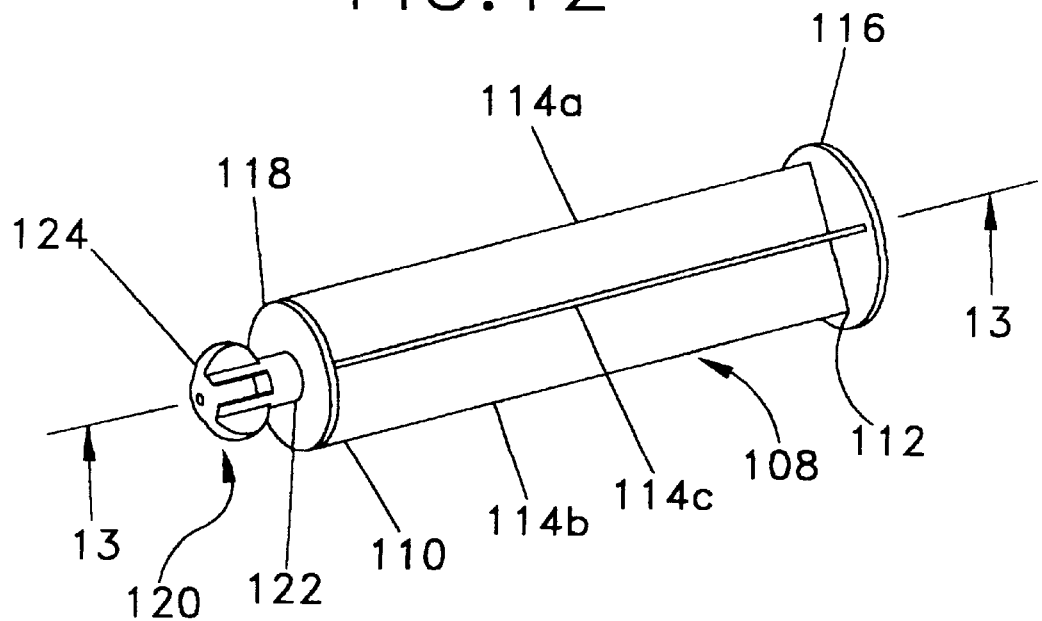
FIG. 12 shows in a perspective view a self-aligning plunger rod of the present invention.
Figure 13:
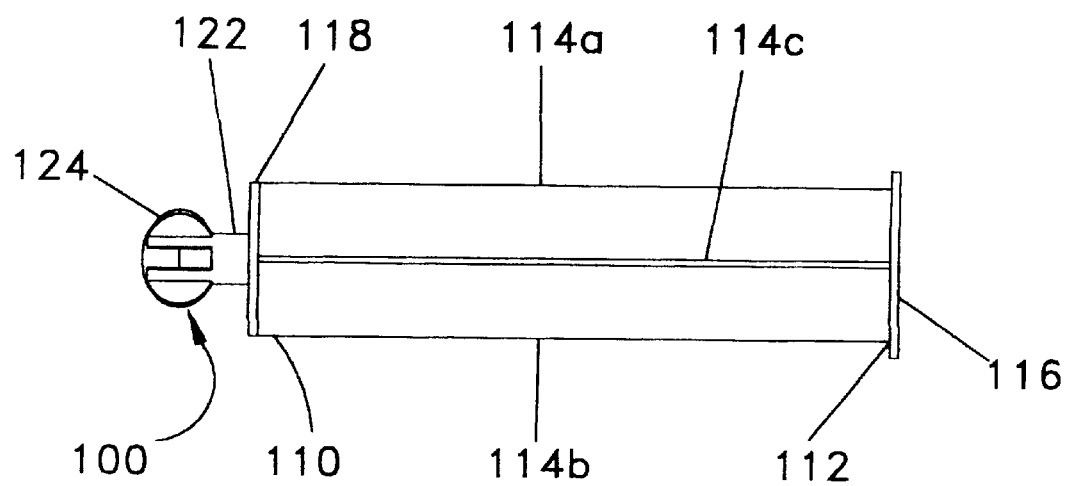
FIG. 13 shows the cross-sectional view thereof taken along the line 13—13.
Figure 14:
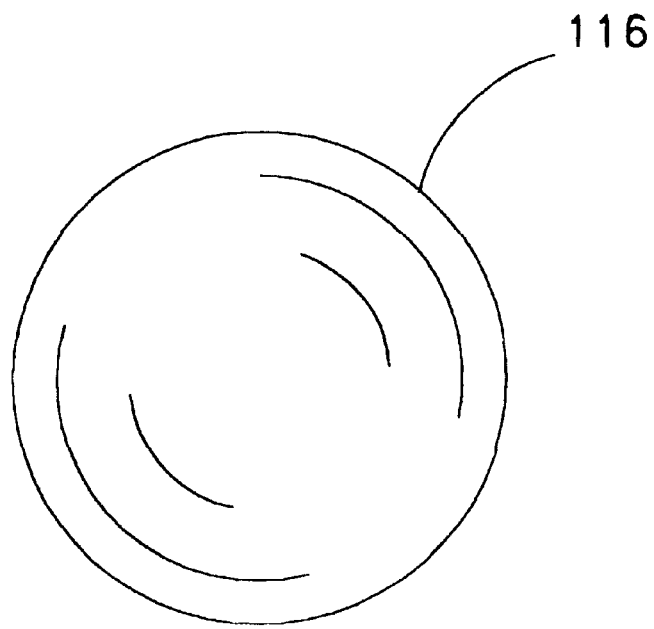
FIG. 14 shows a bottom plan view thereof.
Figure 15:
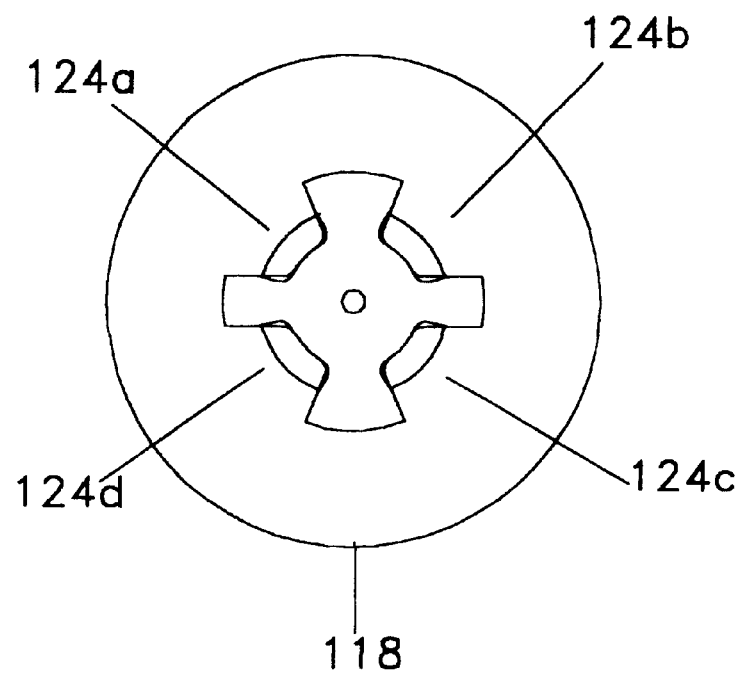
FIG. 15 shows a top plan view thereof.

FIG. 12 is a perspective view of the self-aligning plunger rod 108 of the present invention, and FIG. 13 is a cross-sectional view thereof taken along the line 13—13 of FIG. 12, the self-aligning plunger rod having a distal end 110 and a proximal end 112 comprising: longitudinally extending vanes 114a, 114b, 114c and 114d (114d is hidden); a thumb rest 116 at the proximal end, and a disc 118 at the distal end; and a plunger rod tip 120, generally designated, extending from disc 118 designed to engage a plastic insert. Plunger rod tip is integral with disc 118 and comprises: a neck portion 122 and a ball portion 124, the ball portion having slots 124a, 124b, 124c and 124d therein extending axially from the neck portion.

Figure 16:
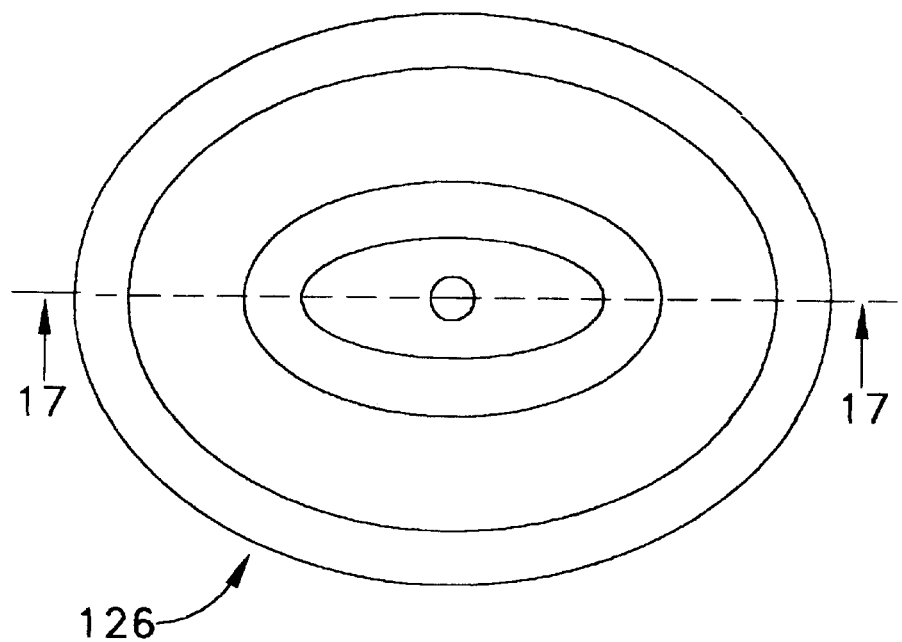
FIG. 16 shows a top plan view of the plastic insert which is to receive the self-aligning plunger rod tip.
Figure 17:
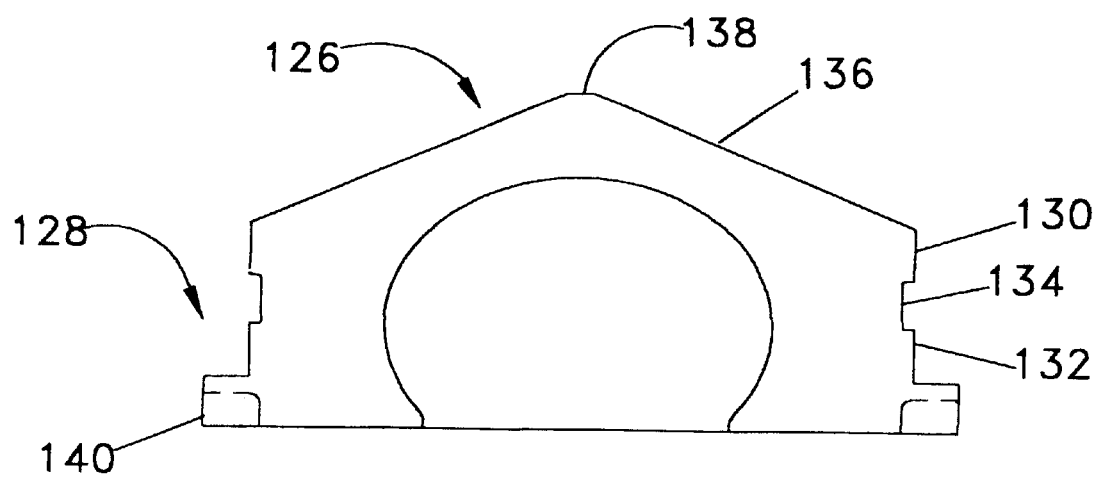
FIG. 17 is a cross-sectional view of the plastic insert taken along the line 17—17 of FIG. 16.

The self-aligning plunger rod 108 of the present invention is used in combination with a plastic insert, the top plan view of which is shown in FIG. 16. The plastic insert is of a generally cone-shaped configuration as best seen in FIG. 17 which is a cross-sectional view of the plastic insert, taken along line 17—17 of FIG. 16. The plastic insert, generally designated by the numeral 126, comprises: ellipsoidal shaft 128 having a distal end 130, and a proximal end 132; between the distal and proximal ends there is provided a cylindrical recess or groove 134; a cone-shaped head 136 extending from distal end 130 and terminating in zenith 138; and an ellipsoidal flange 140 extending from the proximal end 132.

Figure 18:
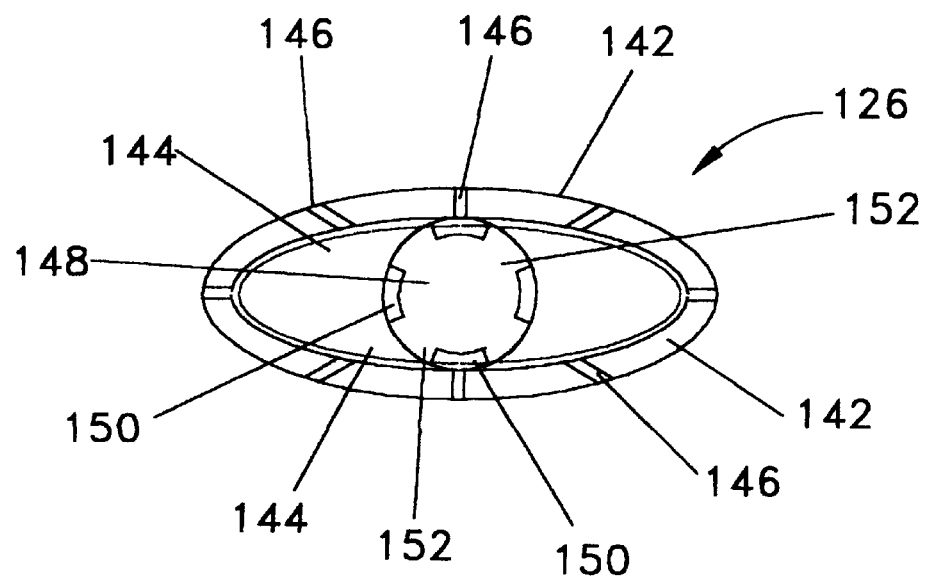
FIG. 18 shows the bottom plan view of the plastic insert.

FIG. 18 shows a bottom plan view of the plastic insert 126, generally designated, which comprises: a first ellipsoidal rim 142 constituting the underside of ellipsoidal flange 140; a second ellipsoidal rim 144 adjacent to said first ellipsoidal rim and projecting slightly above the horizontal surface of the first ellipsoidal rim; a plurality of reinforcing rods 146 connecting the first ellipsoidal rim 142 and the second ellipsoidal rim 144; a cavity 148 defined within said second ellipsoidal rim and the inside surface of the cone-shaped head 136; and a plurality of tabs 150 extending from the second ellipsoidal rim 144 into cavity 148. Between tabs 150 there are notches 152 to receive the slotted ball portion of the plunger rod tip. FIG. 18 also shows: 8 reinforcing rods, however, less than 8 or more than 8 rods may be used; 4 tabs are shown, however, two or three tabs or more than four tabs may be used. Similarly, four slots are shown in FIG. 18 of the ball portion of the plunger rod tip. However, more or less slots may be used as long as the number of slots in the ball portion matches the number of tabs in the plastic insert 126.

Figure 19:
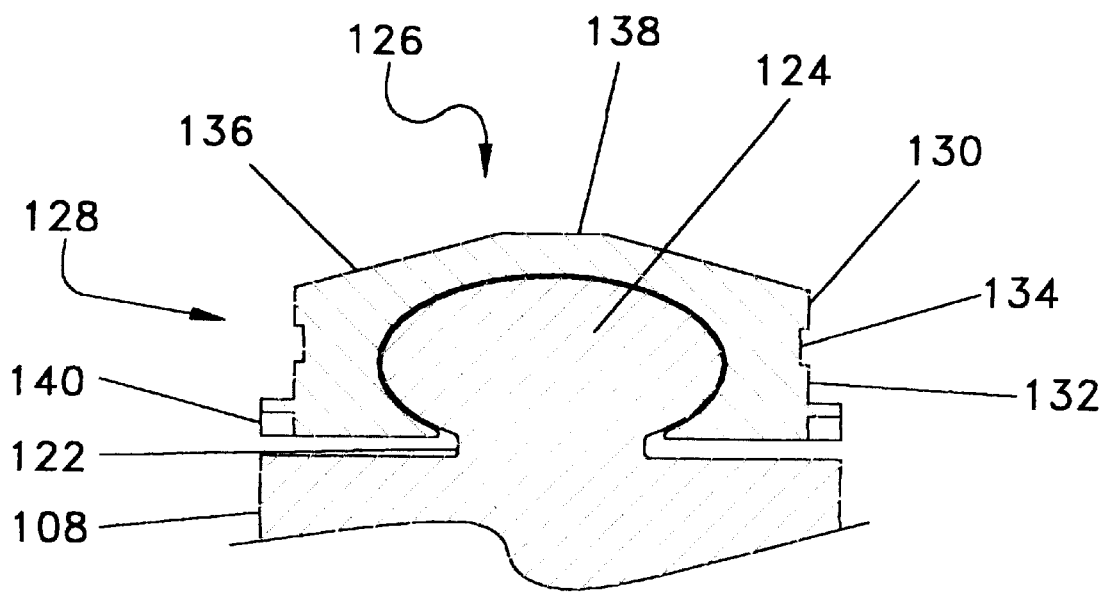
FIG. 19 shows a partial cross-sectional view of the self-aligning plunger rod and plastic insert combination.

FIG. 19 shows, in a partial cross-sectional view, the assembly of the self-aligning plunger rod 108 and the plastic insert combination 126. The ball portion 124 of the plunger rod tip 120 fits into the cavity or socket 148 of the cone-shaped head 136 and freely moves therein, essentially floating within the cavity or socket. Any external pressure on the plunger rod is directed in an axial direction and does not impact the integrity of the seal formed by an elastomeric plunger ring (not shown) and the inside wall of a syringe or cartridge barrel (not shown).

In use, slots 124a, 124b, 124c and 124d of plunger rod tip 120 are aligned with cylindrical openings 154 in the plastic insert 126. The ball portion 124 of the plunger rod tip is inserted into the cavity 148 of the plastic insert. When inserted, the plunger rod is rotated ¼ turn and is held by tabs 150. To remove the plunger rod from the cavity of the plastic insert, the plunger rod is turned ¼ turn forward or backward.

Figure 20:
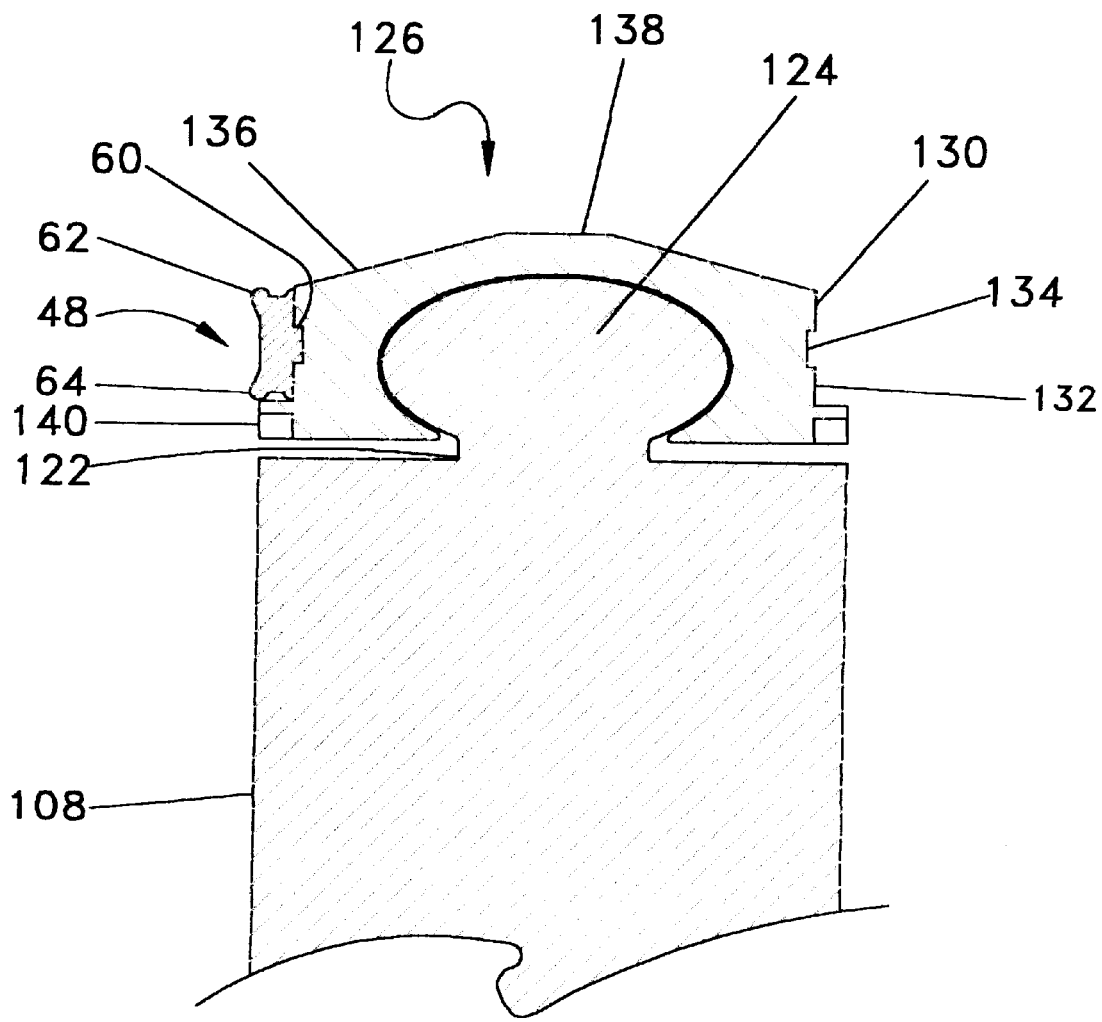
FIG. 20 shows a partial cross-sectional view of the self-aligning plunger rod, plastic insert and plunger ring combination.

FIG. 20 shoes a partial cross-sectional view of the self-aligning plunger rod 108, plastic insert 126, and plunger ring 48 combination.

PARTS LIST

Prior Art

| | |
|---|---|
| Syringe or cartridge barrel | 10 |
| Inner surface of barrel | 12 |
| Cylindrical chamber | 13 |
| Distal end of barrel | 14 |
| Tapered tip of barrel | 15 |
| Proximal end of barrel | 16 |
| Luer collar | 17 |
| Plunger | 18, 18' |
| Plunger rod | 19 |
| Elastomeric closure | 20 |
| Flange on proximal end of barrel | 22 |
| Semi-circular surface of plunger | 23 |
| Medical fluid in syringe barrel | 24 |

Present Invention

| | |
|---|---|
| Cartridge or syringe barrel, generally designated | 30, 30' |
| Inner wall of barrel | 32 |
| Outside wall of barrel | 33 |
| Elliptical chamber | 34 |
| Distal end of barrel | 36 |
| Tapered tip of barrel | 38 |
| Medical fluid in chamber | 39 |
| Luer collar | 40 |
| Proximal end of barrel | 42 |
| Plunger | 44 |
| Flange on proximal end of barrel | 46, 46' |
| Plunger ring, generally designated | 48 |
| Inside wall of plunger ring | 50 |
| Outside wall of plunger ring | 52 |
| Vacant center of plunger ring | 54 |
| Proximal end of plunger ring | 56 |
| Distal end of plunger ring | 58 |
| Internal protuberance on plunger ring | 60 |
| First rim on the outside wall of plunger ring | 62 |
| Second rim on the outside wall of plunger ring | 64 |
| Plunger rod, generally designated | 66 |
| Distal end of plunger rod | 68 |
| Proximal end of plunger rod | 70 |
| Thumb rest of plunger rod | 72 |
| Plunger rod head, generally designated | 74 |
| Tip of plunger rod head | 76 |
| Zenith of plunger rod head tip | 78 |
| Flange of plunger rod head tip | 80 |
| Side portion of plunger rod head | 82 & 86 |
| Recess or groove in side portion | 84 |
| Bottom shoulder of plunger rod head | 88 |

PARTS LIST -continued

| | |
|---|---|
| Plunger rod | 90 |
| Distal end of plunger rod | 92 |
| Proximal end of plunger rod | 94 |
| Thumb rest of plunger rod | 96 |
| Male spiral threads on plunger rod | 98 |
| Plunger rod head | 100 |
| Assembly of plunger rod head with plunger ring | 101 |
| Outside wall of plunger rod head | 102 |
| Recess or groove on the outside wall of plunger rod head | 104 |
| Internal female spiral threads on plunger rod head | 106 |
| Self-aligning plunge rod | 108 |
| Distal end of self-aligning plunger rod | 110 |
| Proximal end of self-aligning plunger rod | 112 |
| Longitudinal extending vanes in plunger rod | 114a, 114b, 114c & 114d |
| Thumb rest at the proximal end | 116 |
| Disc at distal end | 118 |
| Plunger rod tip, generally designated | 120 |
| Neck portion of plunger rod tip | 122 |
| Ball portion of plunger rod tip | 124 |
| Slots in plunger rod tip | 124a, 124b, 124c & 124d |
| Plastic insert, generally designated | 126 |
| Ellipsoidal shaft of plastic insert | 128 |
| Distal end of ellipsoidal shaft | 130 |
| Proximal end of ellipsoidal shaft | 132 |
| Cylindrical recess or groove in ellipsoidal shaft | 134 |
| Cone-shaped head of plastic insert | 136 |
| Zenith of cone-shaped head | 138 |
| Ellipsoidal flange of plastic insert | 140 |
| First ellipsoidal rim of plastic insert | 142 |
| Second ellipsoidal rim of plastic insert | 144 |
| Reinforcing rods in plastic insert | 146 |
| Cavity in plastic insert | 148 |
| Plurality of tabs | 150 |
| Notches between tabs | 152 |

Various modifications of the present invention disclosed will become apparent to those skilled in the art. This invention is intended to include such modifications to be limited only by the scope of the claims.

What is claimed is:

1. A syringe designed for injecting a medical fluid into a site or withdrawing a medical fluid from a site comprising:
   (a) a syringe barrel of ellipsoidal configuration of glass or a polymeric material having an inner surface defining an ellipsoidal chamber having said medical fluid therein, said syringe barrel comprising:
      (1) a distal end terminating in a tapered tip having a bore therethrough encircled by a luer collar to which an injection needle or a connector equipped with a tubing conduit can be attached; and
      (2) a proximal end for receiving a plunger;
   (b) a plunger rod having a stem portion and an ellipsoidal head portion being integral with each other, said head portion being of a rigid, non-elastomeric material having a distal end, a proximal end, and an ellipsoidal shaft therebetween, said ellipsoidal shaft comprising:
      (1) a tip at the distal end thereof adapted to interface said medical fluid contained in the ellipsoidal chamber of said syringe barrel; and
      (2) an exterior surface comprising a groove adapted to receive an elastomeric ring of ellipsoidal configuration;
   (c) said elastomeric ring of ellipsoidal configuration having an inside wall and an outside wall, said inside wall defining a vacant ellipsoidal center, said elastomeric ring being positioned on the exterior surface of the ellipsoidal shaft comprising:

(1) an ellipsoidal protuberance on the inside wall thereof engaging said groove in said ellipsoidal shaft of said plunger rod to form a non-slideable seal therewith; and (2) a plurality of rims on the outside wall of said elastomeric ring for interfacing the inner surface of said ellipsoidal barrel to provide a slideable seal between said plunger and said syringe barrel.

2. The syringe of claim 1 wherein said ellipsoidal head of said plunger rod is made of a thermoplastic material.

3. The syringe of claim 1 wherein said ellipsoidal head portion of said plunger rod is made of a material selected from a group consisting of cyclic olefin copolymers, polymethylpentene, polyethylene, polypropylene, polystyrenes, acrylic polymers and methacrylic polymers.

4. The syringe of claim 1 wherein said elastomeric ring is made of an elastomeric material selected from the group consisting of:

natural rubber;
acrylate-butadiene rubber;
cis-polybutadiene;
chlorobutyl rubber;
chlorinated polyethylene elastomers;
polyalkylene oxide polymers;
ethylene vinyl acetate;
fluorosilicone rubbers;
hexafluoropropylene-vinylidene fluoride-tetrafluoroethylene terpolymers;
butyl rubbers;
polyisobutene;
synthetic polyisoprene rubber;
silicone rubbers;
styrene-butadiene rubbers;
tetrafluoroethylene propylene copolymers; and
thermoplastic-copolyesters.

5. The syringe of claim 4 wherein said elastomeric materials have a durometer of from about 25 to about 80 Shore A.

6. A syringe designed for injecting a medical fluid into a site or withdrawing a medical fluid from a site comprising:

(a) a syringe barrel of ellipsoidal configuration of glass or a polymeric material having an inner surface defining an ellipsoidal chamber containing said medical fluid therein, said syringe barrel having:
  (1) a distal end terminating in a tapered tip having a bore therethrough to which an injection needle or a connector equipped with a tubing conduit can be attached; and
  (2) a proximal end for slideably receiving a plunger of ellipsoidal configuration;

(b) a plunger rod head of ellipsoidal configuration of a rigid, non-elastomeric material having a distal end, a proximal end, and a shaft therebetween, said shaft comprising:
  (1) a tip at the distal end thereof adapted for interfacing said medical fluid contained in said ellipsoidal chamber in said syringe barrel;
  (2) an ellipsoidal inner chamber at the proximal end thereof having female spiral threads therein for engaging spiral male threads of a plunger rod stem;
  (3) an exterior surface having a groove therein adapted to receive an elastomeric ring of ellipsoidal configuration having a protuberance thereon;

(c) said elastomeric ring of ellipsoidal configuration having an inside wall and an outside wall, said inside wall defining a vacant ellipsoidal center, said elastomeric ring being positioned on the exterior surface of said ellipsoidal shaft of said plunger rod head, without covering the tip of the plunger rod head comprising:
  (1) said protuberance on the inside wall of the elastomeric ring of ellipsoidal configuration engaging said groove in the ellipsoidal shaft of said plunger rod head to form a non-slideable seal therewith; and
  (2) a plurality of rims on the outside wall of said elastomeric ring of ellipsoidal configuration for interfacing the inner surface of said syringe barrel to provide a slideable seal between the plunger rod head and the syringe barrel;

(d) a plunger rod stem having a distal end and a proximal end comprising:
  (1) said spiral male threads on the distal end thereof engaging said female spiral threads in the ellipsoidal inner chamber of said plunger rod head; and
  (2) a thumb rest on the proximal end onto which external pressure is applied for injecting said medical fluid into said site, or withdrawing a medical fluid from said site in operating the syringe.

7. The syringe of claim 6 wherein said ellipsoidal plunger head is made of a thermoplastic material.

8. The syringe of claim 6 wherein said ellipsoidal plunger head is made of a material selected from the group consisting of cyclic olefin copolymers, polymethylpentene, polyethylene, polypropylene, polystyrenes, acrylic polymers and methacrylic polymers.

9. The syringe of claim 6 wherein said elastomeric ring is made of an elastomeric material selected from the group consisting of:

natural rubber;
acrylate-butadiene rubber;
cis-polybutadiene;
chlorobutyl rubber;
chlorinated polyethylene elastomers;
polyalkylene oxide polymers;
ethylene vinyl acetate;
fluorosilicone rubbers;
hexafluoropropylene-vinylidene fluoride-tetrafluoroethylene terpolymers;
butyl rubbers;
polyisobutene;
synthetic polyisoprene rubber;
silicone rubbers;
styrene-butadiene rubbers;
tetrafluoroethylene propylene copolymers; and
thermoplastic-copolyesters.

10. The syringe of claim 9 wherein said elastomeric materials have a durometer of from about 25 to about 80 Shore A.

11. A syringe designed for injecting a medical fluid into a site or withdrawing a medical fluid from a site comprising:

(a) a syringe barrel of ellipsoidal configuration of glass or a polymeric material having an inner surface defining an ellipsoidal chamber having said medical fluid therein, said syringe barrel comprising:
  (1) a distal end terminating in a tapered tip having a bore therethrough encircled by a luer collar to which an injection needle or a connector equipped with a tubing conduit can be attached; and
  (2) a proximal end for receiving a plunger;

(b) a plunger rod having a stem portion and an ellipsoidal head portion being integral with each other, said head portion being of a rigid, non-elastomeric material having a distal end, a proximal end, and an ellipsoidal shaft therebetween, said ellipsoidal shaft comprising:
  (1) a tip at the distal end thereof adapted to interface said medical fluid contained in the ellipsoidal chamber of said syringe barrel;
  (2) an exterior surface comprising a groove adapted to receive an elastomeric ring of ellipsoidal configuration; and
  wherein the tip of said ellipsoidal head portion being of a rigid, non-elastomeric material contacts at least 95% of said medical fluid contained in the ellipsoidal chamber of said syringe barrel and said elastomeric ring of ellipsoidal configuration contacts up to 5% of said medical fluid contained in the ellipsoidal chamber of said syring barrel;
(c) said elastomeric ring of ellipsoidal configuration having an inside wall and an outside wall, said inside wall defining a vacant ellipsoidal center, said elastomeric ring being positioned on the exterior surface of the ellipsoidal shaft comprising:
  (1) an ellipsoidal protuberance on the inside wall thereof engaging said groove in said ellipsoidal shaft of said plunger rod to form a non-slideable seal therewith; and
  (2) a plurality of rims on the outside wall of said elastomeric ring for interfacing the inner surface of said ellipsoidal barrel to provide a slideable seal between said plunger and said syringe barrel.

12. A syringe designed for injecting a medical fluid into a site or withdrawing a medical fluid from a site comprising:
(a) a syringe barrel of ellipsoidal configuration of glass or a polymeric material having an inner surface defining an ellipsoidal chamber containing said medical fluid therein, said syringe barrel having:
  (1) a distal end terminating in a tapered tip having a bore therethrough to which an injection needle or a connector equipped with a tubing conduit can be attached; and
  (2) a proximal end for slideably receiving a plunger of ellipsoidal configuration;
(b) a plunger rod head of ellipsoidal configuration a rigid, non-elastomeric material having a distal end, a proximal end, and a shaft therebetween, said shaft comprising:
  (1) a tip at the distal end thereof adapted for interfacing said medical fluid contained in said ellipsoidal chamber in said syringe barrel;
  (2) an ellipsoidal inner chamber at the proximal end thereof having female spiral threads therein for engaging spiral male threads of a plunger rod stem;
  (3) an exterior surface having a groove therein adapted to receive an elastomeric ring of ellipsoidal configuration having a protuberance thereon; and
  wherein the tip of said ellipsoidal head portion being of a rigid, non-elastomeric material contacts at least 95% of said medical fluid contained in the ellipsoidal chamber of said syringe barrel and said elastomeric ring of ellipsoidal configuration contacts up to 5% of said medical fluid contained in the ellipsoidal chamber of said syringe barrel;
(c) said elastomeric ring of ellipsoidal configuration having an inside wall and an outside wall, said inside wall defining a vacant ellipsoidal center, said elastomeric ring being positioned on the exterior surface of said ellipsoidal shaft of said plunger rod head, without covering the tip of the plunger rod head comprising:
  (1) said protuberance on the inside wall of the elastomeric ring of ellipsoidal configuration engaging said groove in the ellipsoidal shaft of said plunger rod head to form a non-slideable seal therewith; and
  (2) a plurality of rims on the outside wall of said elastomeric ring of ellipsoidal configuration for interfacing the inner surface of said syringe barrel to provide a slideable seal between the plunger rod head and the syringe barrel;
(d) a plunger rod stem having a distal end and a proximal end comprising:
  (1) said spiral male threads on the distal end thereof engaging said female spiral threads in the ellipsoidal inner chamber of said plunger rod head; and
  (2) a thumb rest on the proximal end onto which external pressure is applied for injecting said medical fluid into said site, or withdrawing a medical fluid from said site, in operating the syringe.

13. The syringe of claim 12 wherein the ellipsoidal syringe barrel provides an ergonomic grip for a user to apply external pressure upon the thumb rest of the plunger rod stem.

14. A syringe designed for injecting a medical fluid into a site or withdrawing a medical fluid from a site comprising:
(a) a syringe barrel of ellipsoidal configuration of glass or a polymeric material having an inner surface defining an ellipsoidal chamber having said medical fluid therein, said syringe barrel comprising:
  (1) a distal end terminating in a tapered tip having a bore therethrough encircled by a luer collar to which an injection needle or a connector equipped with a tubing conduit can be attached; and
  (2) a proximal end for receiving a plunger;
(b) a plunger rod having a stem portion and an ellipsoidal head portion being integral with each other, said head portion being of a rigid, non-elastomeric material having a distal end, a proximal end, and an ellipsoidal shaft therebetween, said ellipsoidal shaft comprising:
  (1) a tip at the distal end thereof adapted to interface said medical fluid contained in the ellipsoidal chamber of said syringe barrel; and
  (2) an exterior surface comprising a groove adapted to receive an elastomeric ring of ellipsoidal configuration;
(c) said elastomeric ring of ellipsoidal configuration having an inside wall and an outside wall, said inside wall defining a vacant ellipsoidal center, said elastomeric ring being positioned on the exterior surface of the ellipsoidal shaft comprising:
  (1) an ellipsoidal protuberance on the inside wall thereof engaging said groove in said ellipsoidal shaft of said plunger rod to form a non-slideable seal therewith; and
  (2) a plurality of rims on the outside wall of said elastomeric ring for interfacing the inner surface of said ellipsoidal barrel to provide a slideable seal between said plunger and said syringe barrel; and
  wherein reduced running and breakaway forces improve ergonomics of the ellipsoidal syringe barrel.

15. A syringe designed for injecting a medical fluid into a site or withdrawing a medical fluid from a site comprising:
(a) a syringe barrel of ellipsoidal configuration of glass or a polymeric material having an inner surface defining an ellipsoidal chamber containing said medical fluid therein, said syringe barrel having:
  (1) a distal end terminating in a tapered tip having a bore therethrough to which an injection needle or a connector equipped with a tubing conduit can be attached; and (2) a proximal end for slideably receiving a plunger of ellipsoidal configuration;

(b) a plunger rod head of ellipsoidal configuration of a rigid, non-elastomeric material having a distal end, a proximal end, and a shaft therebetween, said shaft comprising:

(1) a tip at the distal end thereof adapted for interfacing said medical fluid contained in said ellipsoidal chamber in said syringe barrel;

(2) an ellipsoidal inner chamber at the proximal end thereof having female spiral threads therein for engaging spiral male threads of a plunger rod stem;

(3) an exterior surface having a groove therein adapted to receive an elastomeric ring of ellipsoidal configuration having a protuberance thereon;

(c) said elastomeric ring of ellipsoidal configuration having an inside wall and an outside wall, said inside wall defining a vacant ellipsoidal center, said elastomeric ring being positioned on the exterior surface of said ellipsoidal shaft of said plunger rod head, without covering the tip of the plunger rod head comprising:

(1) said protuberance on the inside wall of the elastomeric ring of ellipsoidal configuration engaging said groove in the ellipsoidal shaft of said plunger rod head to form a non-slideable seal therewith; and (2) a plurality of rims on the outside wall of said elastomeric ring of ellipsoidal configuration for interfacing the inner surface of said syringe barrel to provide a slideable seal between the plunger rod head and the syringe barrel;

(d) a plunger rod stem having a distal end and a proximal end comprising:

(1) said spiral male threads on the distal end thereof engaging said female spiral threads in the ellipsoidal inner chamber of said plunger rod head; and (2) a thumb rest on the proximal end onto which external pressure is applied for injecting said medical fluid into said site, or withdrawing a medical fluid from said site in operating the syringe; and wherein reduced running and breakaway forces improve ergonomics of the syringe when the external pressure is applied to the thumb rest.

\* \* \* \* \*